United States Patent
Falkel

(10) Patent No.: US 10,952,821 B2
(45) Date of Patent: Mar. 23, 2021

(54) COMBINED ORTHODONTIC MOVEMENT OF TEETH WITH TEMPOROMANDIBULAR JOINT THERAPY

(71) Applicant: uLab Systems, Inc., Menlo Park, CA (US)

(72) Inventor: Michael I. Falkel, Carmel, CA (US)

(73) Assignee: uLab Systems, Inc., San Mateo, CA (US)

( * ) Notice: Subject to any disclaimer, the term of this patent is extended or adjusted under 35 U.S.C. 154(b) by 0 days.

(21) Appl. No.: 15/710,666

(22) Filed: Sep. 20, 2017

(65) Prior Publication Data

US 2018/0078344 A1   Mar. 22, 2018

Related U.S. Application Data

(60) Provisional application No. 62/397,765, filed on Sep. 21, 2016.

(51) Int. Cl.
| | |
|---|---|
| *A61C 7/36* | (2006.01) |
| *A61C 7/08* | (2006.01) |
| *A61C 7/00* | (2006.01) |
| *A61F 5/56* | (2006.01) |
| *A61C 7/10* | (2006.01) |
| *A61F 5/058* | (2006.01) |

(52) U.S. Cl.
CPC .............. *A61C 7/36* (2013.01); *A61C 7/002* (2013.01); *A61C 7/08* (2013.01); *A61C 7/10* (2013.01); *A61F 5/05891* (2013.01); *A61F 5/566* (2013.01); *A61F 2005/563* (2013.01)

(58) Field of Classification Search
CPC ..... A61C 7/08; A61C 7/36; A61F 5/56; A61F 5/566; A61F 5/05891; A61F 2005/563
USPC .................................................. 128/859–862
See application file for complete search history.

(56) References Cited

U.S. PATENT DOCUMENTS

| | | |
|---|---|---|
| 4,068,379 A | 1/1978 | Miller et al. |
| 4,889,485 A | 12/1989 | Iida |
| 4,983,334 A | 1/1991 | Adell |
| 5,055,039 A | 10/1991 | Abbatte et al. |
| 5,186,623 A | 2/1993 | Breads et al. |
| 5,259,762 A | 11/1993 | Farrell |
| 5,691,905 A | 11/1997 | Dehoff et al. |
| 5,975,893 A | 11/1999 | Chishti et al. |
| 6,183,248 B1 | 2/2001 | Chishti et al. |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,250,918 B1 | 6/2001 | Sachdeva et al. |
| 6,299,440 B1 | 10/2001 | Phan et al. |

(Continued)

FOREIGN PATENT DOCUMENTS

| | | |
|---|---|---|
| CA | 2557573 | 7/2012 |
| EP | 1474062 | 4/2011 |

(Continued)

*Primary Examiner* — Edward Moran
(74) *Attorney, Agent, or Firm* — Levine Bagade Han LLP

(57) ABSTRACT

Systems, devices and methods are disclosed for concurrently treating temporomandibular joint dysfunction (TMD) and orthodontically moving teeth. The devices can have an orthodontic aligner and a TMD treatment device. The devices can be configured to concurrently reposition a mandible and orthodontically move one or more teeth.

32 Claims, 6 Drawing Sheets

(56) References Cited

U.S. PATENT DOCUMENTS

| | | |
|---|---|---|
| 6,309,215 B1 | 10/2001 | Phan et al. |
| 6,315,553 B1 | 11/2001 | Sachdeva et al. |
| 6,386,878 B1 | 5/2002 | Pavlovskaia et al. |
| 6,390,812 B1 | 5/2002 | Chishti et al. |
| 6,394,801 B2 | 5/2002 | Chishti et al. |
| 6,398,548 B1 | 6/2002 | Chishti et al. |
| 6,454,565 B2 | 9/2002 | Phan et al. |
| 6,463,344 B1 | 10/2002 | Pavloskaia |
| 6,471,511 B1 | 10/2002 | Chishti et al. |
| 6,485,298 B2 | 11/2002 | Chishti et al. |
| 6,488,499 B1 | 12/2002 | Miller |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,602,070 B2 | 8/2003 | Miller et al. |
| 6,607,382 B1 | 8/2003 | Kuo et al. |
| 6,626,666 B2 | 9/2003 | Chishti et al. |
| 6,629,840 B2 | 10/2003 | Chishti et al. |
| 6,682,346 B2 | 1/2004 | Chishti et al. |
| 6,688,885 B1 | 2/2004 | Sachdeva et al. |
| 6,699,037 B2 | 3/2004 | Chishti et al. |
| 6,702,575 B2 | 3/2004 | Hilliard |
| 6,705,861 B2 | 3/2004 | Chishti et al. |
| 6,705,863 B2 | 3/2004 | Phan et al. |
| 6,722,880 B2 | 4/2004 | Chishti et al. |
| 6,729,876 B2 | 5/2004 | Chishti et al. |
| 6,761,560 B2 | 7/2004 | Miller |
| 6,783,360 B2 | 8/2004 | Chishti |
| 6,786,721 B2 | 9/2004 | Chishti et al. |
| 6,802,713 B1 | 10/2004 | Chishti et al. |
| 6,830,450 B2 | 12/2004 | Knopp et al. |
| 6,846,179 B2 | 1/2005 | Chapouland et al. |
| 6,857,429 B2 | 2/2005 | Eubank |
| 6,886,566 B2 | 5/2005 | Eubank |
| 6,964,564 B2 | 11/2005 | Phan et al. |
| 7,011,517 B2 | 3/2006 | Nicozisis |
| 7,029,275 B2 | 4/2006 | Rubbert et al. |
| 7,037,108 B2 | 5/2006 | Chishti et al. |
| 7,040,896 B2 | 5/2006 | Pavlovskaia et al. |
| 7,056,115 B2 | 6/2006 | Phan et al. |
| 7,059,850 B1 | 6/2006 | Phan et al. |
| 7,063,533 B2 | 6/2006 | Phan et al. |
| 7,074,038 B1 | 7/2006 | Miller |
| 7,077,647 B2 | 7/2006 | Choi et al. |
| 7,092,784 B1 | 8/2006 | Simkins |
| 7,104,790 B2 | 9/2006 | Cronauer |
| 7,121,825 B2 | 10/2006 | Chishti et al. |
| 7,125,248 B2 | 10/2006 | Phan et al. |
| 7,134,874 B2 | 11/2006 | Chishti et al. |
| 7,156,661 B2 | 1/2007 | Choi et al. |
| 7,160,110 B2 | 1/2007 | Imgrund et al. |
| 7,172,417 B2 | 2/2007 | Sporbert et al. |
| 7,192,275 B2 | 3/2007 | Miller |
| 7,220,122 B2 | 5/2007 | Chishti |
| 7,320,592 B2 | 1/2008 | Chishti et al. |
| 7,326,051 B2 | 2/2008 | Miller |
| 7,331,783 B2 | 2/2008 | Chishti et al. |
| 7,347,688 B2 | 3/2008 | Kopelman et al. |
| 7,416,407 B2 | 8/2008 | Cronauer |
| 7,434,582 B2 | 10/2008 | Eubank |
| 7,435,083 B2 | 10/2008 | Chishti et al. |
| 7,442,041 B2 | 10/2008 | Imgrund et al. |
| 7,458,812 B2 | 12/2008 | Sporbert et al. |
| 7,476,100 B2 | 1/2009 | Kuo |
| 7,553,157 B2 | 6/2009 | Abolfathi et al. |
| 7,559,328 B2 | 7/2009 | Eubank |
| 7,578,673 B2 | 8/2009 | Wen et al. |
| 7,590,462 B2 | 9/2009 | Rubbert et al. |
| 7,637,262 B2 | 12/2009 | Bailey |
| 7,641,828 B2 | 1/2010 | Desimone et al. |
| 7,658,610 B2 | 2/2010 | Knopp |
| 7,689,398 B2 | 3/2010 | Cheng et al. |
| 7,717,708 B2 | 5/2010 | Sachdeva et al. |
| 7,771,195 B2 | 8/2010 | Knopp et al. |
| 7,802,987 B1 | 9/2010 | Phan et al. |
| 7,824,180 B2 | 11/2010 | Abolfathi et al. |
| 7,826,646 B2 | 11/2010 | Pavlovskaia et al. |
| 7,841,858 B2 | 11/2010 | Knopp et al. |
| 7,854,609 B2 | 12/2010 | Chen et al. |
| 7,878,801 B2 | 2/2011 | Abolfathi et al. |
| 7,878,804 B2 | 2/2011 | Korytov et al. |
| 7,878,805 B2 | 2/2011 | Moss et al. |
| 7,883,334 B2 | 2/2011 | Li et al. |
| 7,901,207 B2 | 3/2011 | Knopp et al. |
| 7,905,724 B2 | 3/2011 | Kuo et al. |
| 7,914,283 B2 | 3/2011 | Kuo |
| 7,942,672 B2 | 5/2011 | Kuo |
| 7,943,079 B2 | 5/2011 | Desimone et al. |
| 7,957,824 B2 | 6/2011 | Boronvinskih et al. |
| 7,987,099 B2 | 7/2011 | Kuo et al. |
| 8,001,972 B2 | 8/2011 | Eubank |
| 8,021,147 B2 | 9/2011 | Sporbert et al. |
| 8,033,282 B2 | 10/2011 | Eubank |
| 8,038,444 B2 | 10/2011 | Kitching et al. |
| 8,070,487 B2 | 12/2011 | Chishti et al. |
| 8,075,306 B2 | 12/2011 | Kitching et al. |
| 8,099,268 B2 | 1/2012 | Kitching et al. |
| 8,099,305 B2 | 1/2012 | Kuo et al. |
| 8,105,080 B2 | 1/2012 | Chishti et al. |
| 8,123,519 B2 | 2/2012 | Schultz |
| 8,152,518 B2 | 4/2012 | Kuo |
| 8,152,523 B2 | 4/2012 | Sporbert et al. |
| 8,235,713 B2 | 8/2012 | Phan et al. |
| 8,272,866 B2 | 9/2012 | Chun et al. |
| 8,275,180 B2 | 9/2012 | Kuo et al. |
| 8,292,617 B2 | 10/2012 | Brandt et al. |
| 8,303,302 B2 | 11/2012 | Teasdale |
| 8,348,665 B2 | 1/2013 | Kuo |
| 8,356,993 B1 | 1/2013 | Marston |
| 8,401,686 B2 | 3/2013 | Moss et al. |
| 8,401,826 B2 | 3/2013 | Cheng et al. |
| 8,439,672 B2 | 5/2013 | Matov et al. |
| 8,439,673 B2 | 5/2013 | Korytov et al. |
| 8,444,412 B2 | 5/2013 | Baughman et al. |
| 8,465,280 B2 | 6/2013 | Sachdeva et al. |
| 8,469,705 B2 | 6/2013 | Sachdeva et al. |
| 8,469,706 B2 | 6/2013 | Kuo |
| 8,496,474 B2 | 7/2013 | Chishti et al. |
| 8,512,037 B2 | 8/2013 | Andreiko |
| 8,517,726 B2 | 8/2013 | Kakavand et al. |
| 8,535,580 B2 | 9/2013 | Puttler et al. |
| 8,562,337 B2 | 10/2013 | Kuo et al. |
| 8,562,338 B2 | 10/2013 | Kitching et al. |
| 8,562,340 B2 | 10/2013 | Chishti et al. |
| 8,636,509 B2 | 1/2014 | Miller |
| 8,636,510 B2 | 1/2014 | Kitching et al. |
| 8,690,568 B2 | 4/2014 | Chapoulaud et al. |
| 8,708,697 B2 | 4/2014 | Li et al. |
| 8,734,149 B2 | 5/2014 | Phan et al. |
| 8,734,150 B2 | 5/2014 | Chishti et al. |
| 8,738,165 B2 | 5/2014 | Cinader, Jr. et al. |
| 8,765,031 B2 | 7/2014 | Li et al. |
| 8,777,611 B2 | 7/2014 | Cios |
| 8,780,106 B2 | 7/2014 | Chishti et al. |
| 8,807,999 B2 | 8/2014 | Kuo et al. |
| 8,858,226 B2 | 10/2014 | Phan et al. |
| 8,864,493 B2 | 10/2014 | Leslie-Martin et al. |
| 8,899,976 B2 | 12/2014 | Chen et al. |
| 8,899,978 B2 | 12/2014 | Kitching et al. |
| 8,930,219 B2 | 1/2015 | Trosien et al. |
| 8,936,464 B2 | 1/2015 | Kopelman |
| 8,998,608 B2 | 1/2015 | Trosien et al. |
| 8,944,812 B2 | 2/2015 | Kuo |
| 8,961,173 B2 | 2/2015 | Miller |
| 8,986,003 B2 | 3/2015 | Valoir |
| 8,992,215 B2 | 3/2015 | Chapoulaud et al. |
| 9,004,915 B2 | 4/2015 | Moss et al. |
| 9,022,781 B2 | 5/2015 | Kuo et al. |
| 9,026,238 B2 | 5/2015 | Kraemer et al. |
| 9,060,829 B2 | 6/2015 | Sterental et al. |
| 9,107,722 B2 | 8/2015 | Matov et al. |
| 9,119,691 B2 | 9/2015 | Namiranian et al. |
| 9,161,823 B2 | 10/2015 | Morton et al. |

(56) References Cited

U.S. PATENT DOCUMENTS

| | | | |
|---|---|---|---|
| 9,161,824 B2 | 10/2015 | Chishti et al. |
| 9,204,942 B2 | 12/2015 | Phan et al. |
| 9,211,166 B2 | 12/2015 | Kuo et al. |
| 9,241,774 B2 | 1/2016 | Li et al. |
| 9,301,814 B2 | 4/2016 | Kaza et al. |
| 9,320,575 B2 | 4/2016 | Chishti et al. |
| 9,326,830 B2 | 5/2016 | Kitching et al. |
| 9,326,831 B2 | 5/2016 | Cheang |
| 9,333,052 B2 | 5/2016 | Miller |
| 9,345,557 B2 | 5/2016 | Anderson et al. |
| 9,351,809 B2 | 5/2016 | Phan et al. |
| 9,364,297 B2 | 6/2016 | Kitching et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,492,245 B2 | 11/2016 | Sherwood et al. |
| 9,820,829 B2 | 11/2017 | Kuo |
| 9,844,420 B2 | 12/2017 | Cheang |
| 9,922,170 B2 | 3/2018 | Trosien et al. |
| 10,022,204 B2 | 7/2018 | Cheang |
| 10,335,250 B2 | 7/2019 | Wen |
| 10,357,336 B2 | 7/2019 | Wen |
| 10,357,342 B2 | 7/2019 | Wen |
| 10,548,690 B2 | 2/2020 | Wen |
| 10,588,723 B2 | 3/2020 | Falkel |
| 10,631,953 B2 | 4/2020 | Wen |
| 10,642,717 B2 | 4/2020 | Wen |
| 2001/0002310 A1 | 5/2001 | Chishti et al. |
| 2002/0010568 A1 | 1/2002 | Rubbert et al. |
| 2002/0025503 A1 | 2/2002 | Chapoulaud et al. |
| 2002/0042038 A1 | 4/2002 | Miller et al. |
| 2002/0072027 A1 | 6/2002 | Chisti |
| 2002/0094503 A1 | 7/2002 | Chishti et al. |
| 2002/0150859 A1 | 11/2002 | Imgrund et al. |
| 2002/0177108 A1 | 11/2002 | Pavlovskaia et al. |
| 2003/0008259 A1 | 1/2003 | Kuo et al. |
| 2003/0039940 A1 | 2/2003 | Miller |
| 2003/0190576 A1 | 10/2003 | Phan et al. |
| 2003/0207224 A1 | 11/2003 | Lotte |
| 2004/0023188 A1 | 2/2004 | Pavlovskaia et al. |
| 2004/0029068 A1 | 2/2004 | Sachdeva et al. |
| 2004/0038168 A1 | 2/2004 | Choi et al. |
| 2004/0142299 A1 | 7/2004 | Miller |
| 2004/0152036 A1 | 8/2004 | Abolfathi |
| 2004/0166456 A1 | 8/2004 | Chishti et al. |
| 2004/0166462 A1 | 8/2004 | Phan et al. |
| 2004/0166463 A1 | 8/2004 | Wen et al. |
| 2004/0197728 A1 | 10/2004 | Abolfathi et al. |
| 2004/0202983 A1 | 10/2004 | Tricca et al. |
| 2004/0242987 A1 | 12/2004 | Liew et al. |
| 2005/0010450 A1 | 1/2005 | Hultgren et al. |
| 2005/0019721 A1 | 1/2005 | Chishti |
| 2005/0048432 A1 | 3/2005 | Choi et al. |
| 2005/0095552 A1 | 5/2005 | Sporbert et al. |
| 2005/0095562 A1 | 5/2005 | Sporbert et al. |
| 2005/0118555 A1 | 6/2005 | Sporbert et al. |
| 2005/0153255 A1 | 7/2005 | Sporbert et al. |
| 2005/0192835 A1 | 9/2005 | Kuo et al. |
| 2005/0244782 A1 | 11/2005 | Chishti et al. |
| 2005/0271996 A1 | 12/2005 | Sporbert et al. |
| 2006/0003283 A1 | 1/2006 | Miller et al. |
| 2006/0035197 A1 | 2/2006 | Hishimoto |
| 2006/0068353 A1 | 3/2006 | Abolfathi et al. |
| 2006/0078840 A1 | 4/2006 | Robson |
| 2006/0078841 A1 | 4/2006 | Desimone et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0147872 A1 | 7/2006 | Andreiko |
| 2006/0177789 A1 | 8/2006 | O'Bryan |
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2007/0003907 A1 | 1/2007 | Chishti et al. |
| 2007/0238065 A1 | 10/2007 | Sherwood et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |
| 2008/0051650 A1 | 2/2008 | Massie et al. |
| 2008/0057461 A1 | 3/2008 | Cheng et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0118882 A1 | 5/2008 | Su |
| 2008/0141534 A1 | 6/2008 | Hilliard |
| 2008/0182220 A1 | 7/2008 | Chishti et al. |
| 2008/0206702 A1 | 8/2008 | Hedge et al. |
| 2008/0215176 A1 | 9/2008 | Borovinskih et al. |
| 2008/0233530 A1 | 9/2008 | Cinader |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2008/0280247 A1 | 11/2008 | Sachdeva et al. |
| 2008/0305451 A1 | 12/2008 | Kitching et al. |
| 2008/0305453 A1 | 12/2008 | Kitching et al. |
| 2009/0081604 A1 | 3/2009 | Fisher |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1 | 11/2009 | Kuo |
| 2009/0291408 A1 | 11/2009 | Stone-Collonge et al. |
| 2010/0036682 A1 | 2/2010 | Trosien et al. |
| 2010/0055635 A1 | 3/2010 | Kakavand |
| 2010/0173266 A1 | 3/2010 | Lu et al. |
| 2010/0138025 A1 | 6/2010 | Morton et al. |
| 2010/0167225 A1 | 7/2010 | Kuo |
| 2010/0179789 A1 | 7/2010 | Sachdeva et al. |
| 2010/0280798 A1 | 11/2010 | Pattijn et al. |
| 2011/0005527 A1* | 1/2011 | Andrew .............. A61C 7/08 128/848 |
| 2011/0015591 A1 | 1/2011 | Hanson et al. |
| 2011/0020761 A1 | 1/2011 | Kalili |
| 2011/0039223 A1 | 2/2011 | Li et al. |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0165533 A1 | 7/2011 | Li et al. |
| 2011/0269092 A1 | 11/2011 | Kuo et al. |
| 2011/0269097 A1 | 11/2011 | Sporbert et al. |
| 2011/0270588 A1 | 11/2011 | Kuo et al. |
| 2011/0281229 A1 | 11/2011 | Abolfathi |
| 2012/0035901 A1 | 2/2012 | Kitching et al. |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0225401 A1 | 9/2012 | Kitching et al. |
| 2012/0227750 A1* | 9/2012 | Tucker .............. A61F 5/566 128/848 |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0022255 A1 | 1/2013 | Chen et al. |
| 2013/0052625 A1 | 2/2013 | Wagner |
| 2013/0078593 A1 | 3/2013 | Andreiko |
| 2013/0081271 A1 | 4/2013 | Farzin-Nia et al. |
| 2013/0085018 A1 | 4/2013 | Jensen et al. |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1 | 8/2013 | Bailey et al. |
| 2013/0204583 A1 | 8/2013 | Matov et al. |
| 2013/0230819 A1 | 9/2013 | Arruda |
| 2013/0231899 A1 | 9/2013 | Khardekar et al. |
| 2013/0236848 A1 | 9/2013 | Arruda |
| 2013/0266906 A1 | 10/2013 | Soo |

(56) References Cited

U.S. PATENT DOCUMENTS

| | | |
|---|---|---|
| 2013/0302742 A1 | 11/2013 | Li et al. |
| 2013/0308846 A1 | 11/2013 | Chen et al. |
| 2013/0317800 A1 | 11/2013 | Wu et al. |
| 2013/0323665 A1 | 12/2013 | Dinh et al. |
| 2013/0325431 A1 | 12/2013 | See et al. |
| 2014/0023980 A1 | 1/2014 | Kitching et al. |
| 2014/0067335 A1 | 3/2014 | Andreiko et al. |
| 2014/0072926 A1 | 3/2014 | Valoir |
| 2014/0076332 A1 | 3/2014 | Luco |
| 2014/0124968 A1 | 5/2014 | Kim |
| 2014/0172375 A1 | 6/2014 | Grove |
| 2014/0193765 A1 | 7/2014 | Kitching et al. |
| 2014/0193767 A1 | 7/2014 | Li et al. |
| 2014/0229878 A1 | 8/2014 | Wen et al. |
| 2014/0242532 A1 | 8/2014 | Arruda |
| 2014/0255864 A1 | 9/2014 | Machata et al. |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching |
| 2014/0315154 A1 | 10/2014 | Jung et al. |
| 2014/0329194 A1 | 11/2014 | Sachdeva et al. |
| 2014/0349242 A1 | 11/2014 | Phan et al. |
| 2014/0358497 A1 | 12/2014 | Kuo et al. |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0025907 A1 | 1/2015 | Trosien et al. |
| 2015/0044623 A1 | 2/2015 | Rundlett |
| 2015/0044627 A1 | 2/2015 | German |
| 2015/0064641 A1 | 3/2015 | Gardner |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238280 A1* | 8/2015 | Wu .................. A61C 7/002 433/6 |
| 2015/0238282 A1 | 8/2015 | Kuo et al. |
| 2015/0238283 A1 | 8/2015 | Tanugula et al. |
| 2015/0238284 A1* | 8/2015 | Wu .................. A61C 7/36 433/19 |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0305831 A1 | 10/2015 | Cosse |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula et al. |
| 2015/0342464 A1 | 12/2015 | Wundrak et al. |
| 2015/0351871 A1 | 12/2015 | Chishti et al. |
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0074138 A1 | 3/2016 | Kitching et al. |
| 2016/0094670 A1 | 4/2016 | Witte et al. |
| 2016/0095668 A1 | 4/2016 | Kuo et al. |
| 2016/0106521 A1 | 4/2016 | Tanugula et al. |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135926 A1 | 5/2016 | Djamchidi |
| 2016/0135927 A1 | 5/2016 | Boltunov et al. |
| 2016/0157961 A1 | 6/2016 | Lee |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0199216 A1* | 7/2016 | Cam .................. A61F 5/566 128/848 |
| 2016/0203604 A1 | 7/2016 | Gupta et al. |
| 2016/0206402 A1 | 7/2016 | Kitching et al. |
| 2016/0256240 A1 | 9/2016 | Shivapuja et al. |
| 2016/0310235 A1 | 10/2016 | Derakhshan et al. |
| 2016/0338799 A1 | 11/2016 | Wu et al. |
| 2016/0367339 A1 | 12/2016 | Khardekar et al. |
| 2017/0007359 A1 | 1/2017 | Kopelman et al. |
| 2017/0100207 A1 | 4/2017 | Wen |
| 2017/0100208 A1 | 4/2017 | Wen |
| 2017/0100209 A1 | 4/2017 | Wen |
| 2017/0100210 A1 | 4/2017 | Wen |
| 2017/0100211 A1 | 4/2017 | Wen |
| 2017/0100214 A1 | 4/2017 | Wen |
| 2017/0325911 A1 | 11/2017 | Marshall |
| 2018/0014912 A1 | 1/2018 | Radmand |
| 2018/0042708 A1 | 2/2018 | Caron et al. |
| 2018/0078335 A1 | 3/2018 | Falkel |
| 2018/0078343 A1 | 3/2018 | Falkel |
| 2018/0078347 A1 | 3/2018 | Falkel |
| 2018/0092714 A1 | 4/2018 | Kitching et al. |
| 2018/0092715 A1 | 4/2018 | Kitching et al. |
| 2018/0158544 A1 | 6/2018 | Trosien et al. |
| 2018/0168781 A1 | 6/2018 | Kopelman et al. |
| 2019/0008612 A1 | 1/2019 | Kitching et al. |
| 2019/0046297 A1 | 2/2019 | Kopelman et al. |
| 2019/0321135 A1 | 10/2019 | Wen |
| 2019/0343602 A1 | 11/2019 | Wen |
| 2019/0358002 A1 | 11/2019 | Falkel |
| 2020/0146775 A1 | 5/2020 | Wen |
| 2020/0170762 A1 | 6/2020 | Falkel |
| 2020/0205936 A1 | 7/2020 | Wen |
| 2020/0253693 A1 | 8/2020 | Wen |

FOREIGN PATENT DOCUMENTS

| | | |
|---|---|---|
| EP | 2056734 | 9/2015 |
| EP | 2957252 A1 | 12/2015 |
| WO | WO 2001/082192 | 11/2001 |
| WO | WO 2002/047571 | 6/2002 |
| WO | WO 2003/063721 | 8/2003 |
| WO | WO 2004/028391 | 4/2004 |
| WO | WO 2005/086058 | 9/2005 |
| WO | WO 2004/098379 | 11/2005 |
| WO | WO 2006/050452 | 5/2006 |
| WO | WO 2006/096558 | 9/2006 |
| WO | WO 2008/026064 | 3/2008 |
| WO | WO 2008/102132 | 8/2008 |
| WO | WO 2008/149222 | 12/2008 |
| WO | WO 2009/068892 | 6/2009 |
| WO | WO 2016/100577 | 6/2016 |
| WO | WO 2016/004415 | 7/2016 |
| WO | WO 2017/062207 | 4/2017 |
| WO | WO 2017/062208 | 4/2017 |
| WO | WO 2017/062209 | 4/2017 |
| WO | WO 2017/062210 | 4/2017 |
| WO | WO 2018/057622 | 3/2018 |
| WO | WO 2018/118200 | 6/2018 |

* cited by examiner

COMBINED ORTHODONTIC MOVEMENT OF TEETH WITH TEMPOROMANDIBULAR JOINT THERAPY

CROSS-REFERENCE TO RELATED APPLICATION

This application claims priority to U.S. Provisional Application No. 62/397,765 filed Sep. 21, 2016, which is herein incorporated by reference in its entirety for all purposes.

BACKGROUND

1. Technical Field

Systems, devices and methods for treating temporomandibular joint dysfunction (TMD) are disclosed. More specifically, systems, devices and methods are disclosed for treating TMD concurrently with dental and/or orthodontic treatment.

2. Background of the Art

Temporomandibular dysfunction affects a large portion of the population and is regarded as multifactorial condition with a multitude of etiologies and treatment modalities. Some estimates suggest that over 10 million Americans are affected by temporomandibular dysfunction.

The temporomandibular joint (TMJ) is a complex joint that connects the jaw to the temporal bones of the skull. These joints allow movement of the jaw to go up and down and side to side, which facilitates talking, chewing, yawning and the like. Problems with this joint and the muscles of mastication are known as temporomandibular joint disorders (TMDs), although problems with this joint and the associated muscles are sometimes referred to as TMJ disorders as well. TMD occurs where the mandibular condyle does not sit or move properly in the glenoid fossa of the petrous portion of the temporal bone.

There are many different causes of TMD, for example, trauma, whiplash, arthritis, dislocation of the cartilage disc in the joint, stress, clenching or grinding of the teeth, or malocclusions. Dentistry and orthodontics can also cause symptoms of TMD to manifest.

TMD symptoms can range from slight to debilitating, including, for example, wearing of the teeth, clicking, popping, or grating of the TMJ (e.g., when opening or closing the mouth), internal derangement of the joint (e.g., displaced disc, dislocated jaw, or injury to the mandibular condyle), headaches, myofascial pain, radiating pain in the face, jaw, or neck, stiffness in the jaw, limited movement or locking of the jaw, arthritis, and malocclusions.

There are many different schools of thought with respect to treatment modalities for TMD within the medical and dental profession. As many of these treatment modalities involve various appliances that cover the teeth and take the pressure off the joint and muscles, the ultimate goal is to treat TMD patients with a TMD appliance to the point where they are no longer dependent on appliance therapy.

Current TMD treatment modalities include various TMD appliances that adjust the position of the jaw, for example, mandibular advancement appliances (e.g., Herbst appliances, elastic mandibular advancement (EMA) appliances), stabilization splints (e.g., nightguards, day guards), and deprogrammers. Current modalities also include orthodontically moving the teeth. However, no treatment modality currently exists that simultaneously moves teeth and provides TMD treatment that is separate and apart from the orthodontic movement of teeth (e.g., via braces or a retainer). A need therefore exists to address this deficiency, as TMD appliances, when used separately from orthodontic treatments that move teeth, can cause teeth to shift and compel subsequent orthodontic treatment to correct the resulting malocclusions, and orthodontic treatments that move teeth, when used separately from TMD appliances, can cause TMD even though the orthodontic movement of teeth can treat TMD. Further, since TMD appliances cause teeth to move, current TMD appliances become nonfunctional as soon as the teeth move, for example, into new positions that can in turn cause new TMD issues. The new TMD issues either require the teeth to be orthodontically moved, and/or the use of a second (e.g., new) TMD appliance to accommodate the shifted teeth. Accordingly, a need currently exists to combine the two modalities, i.e., to combine the orthodontic movement of teeth with TMD appliance therapy.

The present disclosure addresses this need by combining orthodontic and TMD treatments, including malocclusion correction and/or bite maintenance (e.g., preventative treatment that inhibits one or more teeth from moving into a malocclusion position, and/or that encourages one or more teeth to move into a new position that will accommodate the resultant TMD therapy position). Simultaneously (as opposed to incidentally and/or sequentially) orthodontically moving teeth and providing TMD appliance therapy can advantageously ease or eliminate symptoms associated with TMD, shorten the length of TMD treatment, and reduce the cost of TMD treatment, all while attaining a desirable therapeutic result that reduces or eliminates the need to seesaw back and forth between TMD appliance therapy and the orthodontic movement of teeth to sequentially correct the problems that each treatment modality causes when used separately.

The present disclosure simultaneously considers TMJ position and occlusion while treating both, with the end result being a patient with a pain free smile. By combining orthodontic and TMD treatments, the combined therapy results in ideal dental, muscular and joint position at the completion of treatment, as opposed to only dental position or only joint position as is the case with the current modalities that are used separately.

Comprehensive dental treatments should include consideration of the structures involved, including the TMJ, muscles of mastication, teeth and gums. The present disclosure allows the dental provider to combine TMD therapy and orthodontic treatment to end with a result that the patient considers a beautiful smile with harmonious joint and muscles. For example, the present disclosure allows for numerous different TMD treatment modalities to be treated with orthodontic aligners simultaneously. The TMD treatment modalities can include mandibular advancement style appliances and/or palatal and mandibular expanders using the orthodontic aligners. By manipulating the 3D models the aligners can act both as orthodontic movers of teeth along with ideal positioning of the TMJ and muscle.

A need exists to combine orthodontic and/or dental treatment with TMD appliances. The advantages of combining these modalities include: (1) moving and/or maintaining the teeth into a position that accommodates the new TMD treatment position of the lower jaw, (2) existing TMD devices and appliances can cause malocclusions to develop which by design can be prevented or otherwise mitigated with the oral appliances disclosed herein, (3) the oral appliances disclosed herein can be titrated over a series of two or more steps for ideal mandibular advancement and/or opening and for the ideal orthodontic movement of teeth with software, and/or (4) the oral appliances disclosed herein can allow free mandibular motion while having the ability to hold the joint in a fixed position if necessary for the desired treatment or comfort of the patient.

BRIEF SUMMARY OF THE INVENTION

This disclosure relates generally to the combined orthodontic movement and/or dental treatment of teeth and TMD treatment.

More specifically, orthodontic and/or dental TMD treatment systems, apparatuses and methods of using the same are disclosed. The TMD treatment systems and apparatuses disclosed can concurrently move teeth and treat TMD. The TMD treatment systems and apparatuses disclosed can concurrently advance the mandible and move teeth. The TMD treatment systems and apparatuses disclosed can concurrently expand the hard and/or soft palate and move teeth. The TMD treatment systems and apparatuses disclosed can concurrently whiten and/or move teeth and treat TMD. The TMD treatment systems and apparatuses disclosed can concurrently clean and/or move teeth and treat TMD. The TMD treatment systems apparatuses disclosed can concurrently move teeth, advance the mandible, expand the hard and/or soft palate, whiten teeth, apply hygienic treatment, treat TMD, or any combination thereof.

The TMD treatment systems and apparatuses can have dental trays and/or orthodontic aligner trays. The TMD treatment systems apparatuses can have craniofacial adjustment blocks. The craniofacial adjustment blocks can be attached to or integrated with one or more trays (e.g., aligners).

Oral appliances are disclosed for the combined orthodontic movement of teeth and treatment of temporomandibular joint dysfunction (TMD). For example, an oral appliance is disclosed that can have an orthodontic aligner and a TMD treatment device. The oral appliance can be configured to concurrently reposition a mandible and orthodontically move one or more teeth.

Systems for the combined orthodontic movement of teeth and treatment of temporomandibular joint dysfunction (TMD) are disclosed. For example, a system is disclosed that can have a series of oral appliances. The series of oral appliances can be configured to concurrently reposition both a mandible and orthodontically move one or more teeth. Each oral appliance in the series can have an orthodontic tray and a TMD treatment device.

Methods of progressively treating temporomandibular joint dysfunction (TMD) are disclosed. For example, a method is disclosed that can include providing a series of oral appliances. The series of oral appliances can be configured to concurrently reposition both a mandible and orthodontically move one or more teeth. Each oral appliance in the series can have an orthodontic tray and a TMD treatment device.

BRIEF DESCRIPTION OF THE DRAWINGS

The drawings shown and described are exemplary embodiments and non-limiting. Like reference numerals indicate identical or functionally equivalent features throughout.

DETAILED DESCRIPTION

Figure 1:
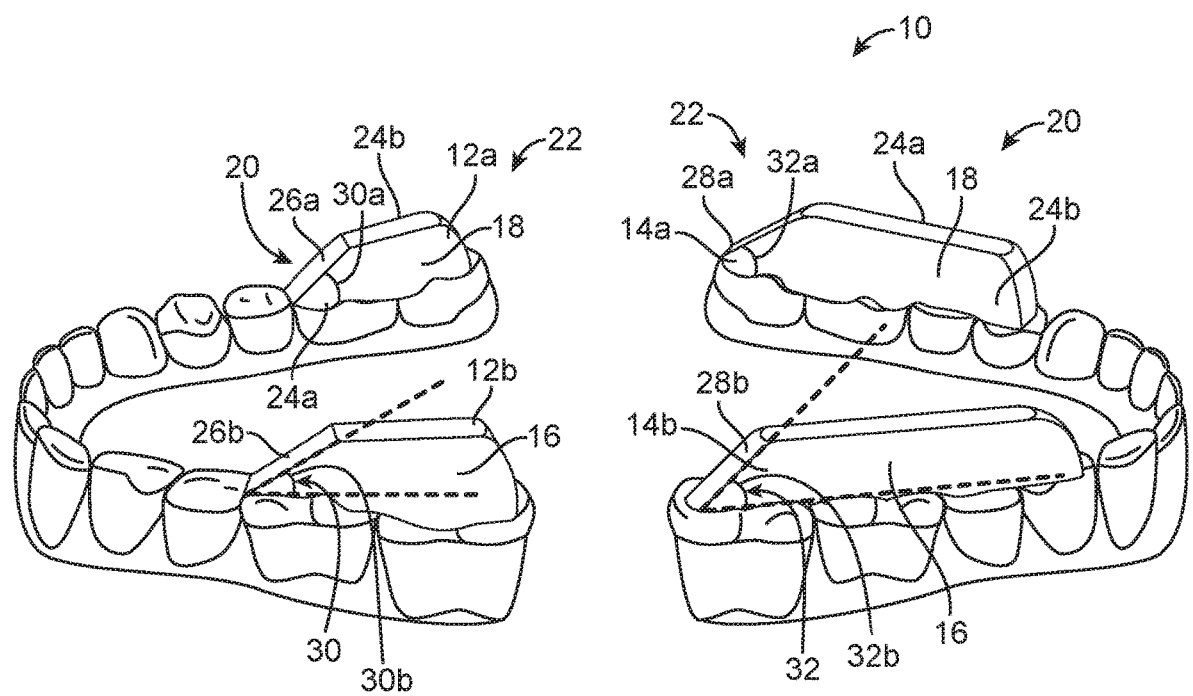
FIG. 1 illustrates isometric views of a variation of craniofacial adjustment blocks of an oral appliance.

Systems, devices and methods are disclosed that can concurrently apply TMD treatment, apply orthodontic treatment, apply dental treatment, or any combination thereof. The systems, devices and methods disclosed can apply orthodontic treatment to any craniofacial structure, including the dentition, the palate, the maxilla, the mandible, or any combination thereof. The systems, devices and methods disclosed can apply any dental treatment to the teeth, including whitening treatments, cleaning treatments, gingival recession treatments, or any combination thereof. For example, systems, devices and methods are disclosed that can concurrently move one or more teeth, advance the mandible, retrude the mandible, expand the hard and/or soft palate, whiten teeth, clean teeth, treat gum line recession, reshape the airway, maintain the airway, or any combination thereof.

The disclosed systems, devices and methods can treat TMD by manipulating one or more craniofacial structures. TMD can be treated by repositioning the jaw and/or by adjusting the bite, for example, by widening the dental arches, by increasing the interocclusal distance between the upper and lower teeth and/or by advancing the lower jaw. The position of the jaw can be adjusted concurrently with the orthodontic treatment of, for example, misaligned teeth, malocclusions, and/or narrow arches. Additionally or alternatively, the position of the jaw can be adjusted concurrently with a teeth whitening, cleaning and/or gingival recession treatment.

More particularly, oral appliances are disclosed that can reposition the jaw and/or adjust the bite to treat TMD. The oral appliances disclosed can also reshape and/or maintain the airway to treat sleep breathing disorders (SBD) such as obstructive sleep apnea (OSA) and snoring. The oral appliances disclosed can reposition the jaw, adjust the bite, and/or reshape the airway by simultaneously manipulating one or more craniofacial structures and moving teeth, cleaning teeth, whitening teeth, or any combination thereof. The oral appliances disclosed can treat TMD, SBD, and snoring with various orthodontic treatment modalities, for example, mandibular advancement and/or palatal expansion. The oral appliances disclosed can simultaneously provide both orthodontic and TMD treatment and result in more properly aligned teeth and a reduction or elimination in TMD symptoms. The oral appliances disclosed can simultaneously provide orthodontic, TMD, and SBD treatment and result in more properly aligned teeth, a reduction or elimination in TMD symptoms, and/or a more open airway. The oral appliances disclosed can simultaneously provide dental whitening, dental cleaning and/or gingival recession treatments in combination with TMD and/or SBD treatment and result in whiter teeth, cleaner teeth, healthier gums, fresher breath, a reduction or elimination in TMD symptoms, and/or a more open airway.

System and Apparatus

TMD appliance therapy can be combined with the orthodontic movement of teeth, for example, with orthodontic aligner treatment. For example, TMD appliances such as mandibular advancement appliances (e.g., Herbst appliances, elastic mandibular advancement (EMA) appliances), stabilization splints (e.g., nightguards, day guards), deprogrammers (e.g., anterior deprogrammers), flat planes, and full contact splints with anterior guidance can be used and combined with, attached to, removably attached to, integrated with, or have oral tray aligners that can orthodontically move teeth concurrently with TMD treatment. The TMD appliances can provide TMJ positioning that allows both the jaw to move and that holds the jaw in position during treatment, for example, within a movement range such that movement of the jaw is permitted but constrained, or such that movement of the jaw is not permitted and completely constrained.

The TMD appliances disclosed can simultaneously reposition the jaw and orthodontically move teeth, for example, by virtue of their combination with aligner treatment. The systems disclosed however, not only simply allow for their combination, the systems also advantageously allow for their treatments to be coordinated with one another. For example, the movement of one or more teeth that the TMD aligners disclosed (e.g., the combination of a TMD device and an orthodontic aligner) can cause is separate from the movement of teeth that TMD appliances otherwise solely cause without the use of concurrent aligner treatment. For example, whereas the aligner treatment that this disclosure combines with TMD appliances causes one or more teeth to move into a desired or a more desirable position, current TMD appliances without the combined aligner treatment cause teeth to move into an undesired or a less desirable position. The orthodontic/TMD appliances disclosed avoid such undesired concomitant movement associated with solo TMD appliance use by orthodontically moving the teeth into a position that is physiologically correct for the TMJ and musculature during TMD treatment with a TMD appliance. Custom TMD appliances can be attached to or integrated with orthodontic tray aligners as well. TMD appliances and orthodontic tray aligners can be monolithically formed, or can be assembled from one or more parts.

The orthodontic movement of teeth can include malocclusion correction (e.g., moving one or more teeth into a new position, including into a final position and/or into one or more intermediate positions prior to the final position) and/or bite maintenance (e.g., preventative treatment that inhibits one or more teeth from moving into a malocclusion position, and/or that encourages one or more teeth to move into a new position that will accommodate the resultant TMD therapy position, or that will accommodate the final TMJ position that is desired). Simultaneously (as opposed to sequentially) orthodontically moving teeth and providing TMD appliance therapy can advantageously ease or eliminate symptoms associated with TMD, shorten the length of TMD treatment, and reduce the cost of TMD treatment, all while attaining a desirable therapeutic result that reduces or eliminates the need to seesaw back and forth between TMD appliance therapy and the orthodontic movement of teeth to sequentially correct the problems that each treatment modality causes when used separately.

For example, FIG. 1 illustrates a variation of a customizable oral appliance 10 for treating TMD. The oral appliance 10 can be a stabilization splint that can stabilize the mandible in one or more positions. For example, the oral appliance 10 can be a stabilization splint that can advance the mandible, for example, by stabilizing the mandible in a forward position. The appliance 10 can have one or more maxillary blocks 12 and one or more mandibular blocks 14. The maxillary and mandibular blocks 12, 14 are also referred to as guides, craniofacial adjustment blocks, and TMD components (both individually and collectively) throughout. For example, the appliance 10 can have 1 to 6 maxillary blocks 12 and 1 to 6 mandibular blocks 14. The number of maxillary blocks 12 can be less than, equal to, or greater than the number of mandibular blocks 14. For example, FIG. 1 illustrates that the appliance 10 can have two maxillary blocks 12 and two mandibular blocks 14. As another example, the appliance 10 can have one maxillary block 12 and two mandibular blocks 14 or vice versa. The appliance 10 can have one, two, three, four, or five more maxillary blocks 12 than mandibular blocks 14 or vice versa. The appliance 10 can have one or more maxillary blocks 12 and no mandibular blocks 14 or one or more mandibular blocks 14 and no maxillary blocks 12. The blocks 12, 14 can be placed in a person's oral cavity.

FIG. 1 illustrates that the appliance 10 can have a first maxillary block 12a and a second maxillary block 12b. Anatomically, the maxillary first block 12a can be a left block and the maxillary second block 12b can be a right block, or vice versa. The maxillary first and second blocks 12a, 12b can be configured to be placed on a lateral left and right side, respectively, of a maxillary dental arch. The appliance 10 can have a first mandibular block 14a and a second mandibular block 14b. Anatomically, the mandibular first block 14a can be a left block and the mandibular second block 14b can be a right block, or vice versa. The mandibular first and second blocks 14a, 14b can be configured to be placed on a lateral left and right side, respectively, of a mandibular dental arch.

FIG. 1 illustrates that the blocks 12, 14 can each have a buccal side 16, a lingual side 18, an anterior portion 20, a posterior portion 22 and teeth surfaces 24. Each maxillary block 12 can have a maxillary tooth surface 24a and/or a mandibular tooth surface 24b. Each mandibular block 14 can have a maxillary tooth surface 24a and/or a mandibular tooth surface 24b. The surfaces 24 can conform to surfaces of the teeth and/or can have a geometry to orthodontically move one or more teeth from one position to another. One or more of the surfaces 24 of maxillary and mandibular blocks can be configured to have a friction fit over a portion of one or more teeth.

The maxillary tooth surfaces 24a of the maxillary blocks 12 can have a surface geometry configured to move one or more maxillary teeth from a first position to a second position. The mandibular tooth surfaces 24b of the maxillary blocks 12 can be flat (e.g., as shown in FIG. 1) or can have a surface geometry configured to move one or more mandibular teeth from a first position to a second position. The mandibular tooth surfaces 24b of the mandibular blocks 14 can have a surface geometry configured to move one or more mandibular teeth from a first position to a second position. The maxillary tooth surfaces 24a of the mandibular blocks 14 can be flat (e.g., as shown in FIG. 1) or can have a surface geometry configured to move one or more maxillary teeth from a first position to a second position.

A series of blocks 12, 14 can be designed to progressively reposition the maxillary and/or mandibular teeth in two or more successive steps, for example, as disclosed in PCT Publication WO 2016/004415 and U.S. application Ser. No. 15/386,280 (published as US 2017/0100214) in relation to orthodontic trays, both of which are herein incorporated by reference in their entireties for all purposes. Each block 12, 14 in a series can have a surface 24 that has a geometry that corresponds to an intermediate or end tooth arrangement intended for the block 12, 14 in the series. The blocks 12, 14 can be sufficiently resilient to accommodate or conform to misaligned teeth, but apply sufficient force against the misaligned teeth to reposition the teeth to the intermediate or end arrangement as desired for the particular treatment step. A series of blocks 12, 14 can have geometries selected to progressively reposition teeth from a first arrangement through one or more successive intermediate arrangements to a final arrangement. Each block in the series can have the same or different dimensions than one or more other blocks in the series, as described below. A series of blocks 12, 14 can have 1 to 100 maxillary blocks 12 and 1 to 100 mandibular blocks 14, for example, 1 to 55 maxillary blocks 12 and 1 to 55 mandibular blocks 14, 1 to 50 maxillary blocks 12 and 1 to 50 mandibular blocks 14, 1 to 45 maxillary blocks 12 and 1 to 45 mandibular blocks 14, 1 to 40 maxillary blocks 12 and 1 to 40 mandibular blocks 14, less than 40 maxillary blocks 12 and less than 40 mandibular blocks, or any combination thereof. For example, a series of blocks can have 40, 41, 42, 43, 44, 45, 46, 47, 48, 49, or 50 maxillary blocks 12 and 40, 41, 42, 43, 44, 45, 46, 47, 48, 49, or 50 mandibular blocks 14. The number of maxillary blocks 12 can be the same or different as the number mandibular blocks 14 in a series.

FIG. 1 illustrates that the maxillary blocks 12 can each have one or more maxillary block guide surfaces 26 (e.g., 1 to 6 or more maxillary guide surfaces 26) and that the mandibular blocks 14 can each have one or more mandibular block guide surfaces 28 (e.g., 1 to 6 or more mandibular guide surfaces 28). The guide surfaces 26, 28 are variously referred to throughout as ramps, stops, disclusion surfaces, expansion surfaces, resting surfaces and/or other similar terms. The guide surfaces 26 can be on any part or define any surface of the blocks 12, 14, for example, the anterior and/or posterior portions 20, 22 of the maxillary and mandibular blocks 12, 14.

FIG. 1 illustrates that the anterior portion 20 of the maxillary blocks 12 can have one maxillary guide surface 26 and that the posterior portion 22 of the mandibular blocks 14 can have one mandibular guide surface 28. For example, FIG. 1 illustrates that the maxillary first and second blocks 12a, 12b can have maxillary first and second guide surfaces 26a, 26b, respectively, and that the mandibular first and second blocks 14a, 14b can have mandibular first and second guide surfaces 28a, 28b, respectively. The exact number and orientation of the guide surfaces 26, 28 can be customizable and depend on a person's tolerance for the blocks 12, 14, craniofacial structure, teeth alignment, orthodontic treatments being applied, TMD treatment being applied, dental treatment being applied or any combination thereof, each factor being critical to the design of the blocks 12, 14. Each block in a series can have the same or different number and/or orientation of guide surfaces 28a, 28b as one or more other blocks in the series.

While FIG. 1 illustrates that the anterior portions 20 of the maxillary blocks 12 and the posterior portions 22 of the mandibular blocks 14 have the guide surfaces 26, 28 (e.g., guide surfaces 26a, 26b, 28a, 28b), the anterior and/or posterior portion 20, 22 of each of the maxillary and mandibular blocks can have one or more guide surfaces in addition to or in lieu of the guide surfaces 26, 28 shown in FIG. 1. For example, the posterior portions 22 of the maxillary blocks 12 can have guide surfaces and/or the anterior portions 20 of the mandibular blocks 14 can have guide surfaces. However, the anterior and/or posterior portions 20, 22 of the maxillary and/or mandibular blocks 12 need not have a guide surface. For example, FIG. 1 illustrates that the posterior portions 22 of the maxillary blocks 12 and the anterior portions 20 of the mandibular blocks 14 can have ends that do not have a guide surface. FIG. 1 illustrates that the ends of the posterior portions 22 of the maxillary blocks 12 and the anterior portions 20 of the mandibular blocks 14 can have a flat or curved surface with a portion that is perpendicular or nearly perpendicular to an occlusal plane.

Each guide surface (e.g., guide surfaces 26, 28) can be paired with an opposing (also referred to as cooperating, interacting, engaging, contacting, or interfering) guide surface. For example, the blocks 12, 14 can be paired such that their corresponding guide surfaces 26, 28 form one or more corresponding guide surfaces pairs 26-28. Each guide surface in a guide surface pair can be configured to interact with its opposing guide surface. For example, the opposing guide surfaces of a guide surface pair 26-28 can be configured to slidably engage or otherwise move relative to one another and/or be configured to rest against each other or otherwise inhibit or prevent movement relative to one another. At least a portion of each guide surface, including the entire guide surface, can be configured to contact at least a portion of its opposing guide surface, including the entire opposing guide surface, such that any portion 100% or less is appreciated. FIG. 1 illustrates that the two left blocks 12a, 14a can form a left guide surface pair 26a-28a and that the two right blocks 12b, 14b can form a right guide surface pair 26b-28b. The maxillary and mandibular guide surfaces 26a, 28a of the left pair 26a-28a can be designed to interact with each other and the maxillary and mandibular guide surfaces 26b, 28b of the right pair 26b-28b can be designed to interact with each other. Each guide surface 26, 28 can interact with its opposing guide surface in a self-guided manner. The guide surfaces 26, 28 can position the mandible in a joint position that treats TMD (e.g., a joint position that relieves or eliminates TMD symptoms) while the teeth are moving or otherwise encouraged to move orthodontically.

Each guide surface 26, 28 can be or have one or more planar surfaces (e.g., 1 to 50 planar surfaces). For example, FIG. 1 illustrates that each guide surface 26, 28 can have one planar surface. However, the guide surfaces 26, 28 can have any surface geometry, including planar, curved (e.g., one or more concave and/or convex portions), polygonal (e.g., any combination of two or more planes), irregular, or any combination thereof. Thus, although the guide surfaces 26, 28 can function as guide planes and may be planar in general characteristics, strict conformity with flatness associated with a plane is not required.

The guide surfaces 26, 28 can be angled such that they define one or more inclined, horizontal, and/or declined planar surfaces. The guide surfaces 26, 28 can be at one or more angles relative to, for example, a reference plane, reference surface, or reference axis. FIG. 1 illustrates that the maxillary guide surfaces 26 (e.g., the maxillary first and second guide surfaces 26a, 26b) can each be at maxillary guide surface angle 30. The maxillary guide surface angle 30 can be the angle formed between the maxillary guide surfaces 26 and a reference plane, reference surface, or reference axis such as the maxillary tooth surface 24*a* (or an occlusal plane), maxillary orthodontic aligner (not shown), or any combination thereof. The maxillary guide surface angle 30 can be from about 0 degrees to about 90 degrees or more broadly from about 0 degrees to about 150 degrees. For angles greater than 90 degrees, the maxillary guide surface 26 can face toward as opposed to away from the maxillary dentition. For example, the maxillary guide surface angle 30 can be from about 15 degrees to about 75 degrees, from about 40 degrees to about 50 degrees, from about 30 degrees to about 60 degrees, from about 20 degrees to about 70 degrees, or from about 10 degrees to about 80 degrees, including every 1 degree increment within these ranges; for example, the maxillary guide surface angle 30 can be about 0 degrees, about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 130 degrees, about 135 degrees, about 140 degrees, about 145 degrees, or about 150 degrees. Angles within these ranges and/or having these values can advantageously allow the maxillary and mandibular blocks 12, 14 to slidably engage or otherwise move relative to one another and/or rest against each other or otherwise inhibit or prevent movement relative to one another. Angles within these ranges and/or having these values can advantageously allow the maxillary and mandibular blocks 12, 14 to contact (e.g., slidably contact) each other to move and/or maintain the mandible into a forward position and/or to increase and/or maintain the interocclusal separation between the maxillary and mandibular dental arches. Angles within these ranges and/or having these values can therefore advantageously facilitate treating TMD by repositioning the jaw and/or by adjusting the bite. Angles within these ranges and/or having these values can also facilitate the reshaping of the airway into a more open configuration (e.g., from a less open first configuration to a more open second configuration). Each maxillary block 12 in a series can have the same or different maxillary guide surface angle 30 as one or more other maxillary blocks 12 in the series.

FIG. 1 illustrates that the mandibular guide surfaces 28 (e.g., the mandibular first and second guide surfaces 28*a*, 28*b*) can each be at a mandibular guide surface angle 32. The mandibular guide surface angle 32 can be the angle formed between the mandibular guide surfaces 28 and a reference plane, reference surface, or reference axis such as the mandibular tooth surface 24*b* (or an occlusal plane), mandibular orthodontic aligner (not shown), or any combination thereof. The mandibular guide surface angle 32 can be from about 0 degrees to about 90 degrees or more broadly from about 0 degrees to about 150 degrees. For angles greater than 90 degrees, the mandibular guide surface 28 can face toward as opposed to away from the mandibular dentition. For example, the mandibular guide surface angle 32 can be from about 15 degrees to about 75 degrees, from about 40 degrees to about 50 degrees, from about 30 degrees to about 60 degrees, from about 20 degrees to about 70 degrees, or from about 10 degrees to about 80 degrees, including every 1 degree increment within these ranges; for example, the mandibular guide surface angle 32 can be about 0 degrees, about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, about 130 degrees, about 135 degrees, about 140 degrees, about 145 degrees, or about 150 degrees. Angles within these ranges and/or having these values can advantageously allow the maxillary and mandibular blocks 12, 14 to slidably engage or otherwise move relative to one another and/or rest against each other or otherwise inhibit or prevent movement relative to one another. Angles within these ranges and/or having these values can advantageously allow the maxillary and mandibular blocks 12, 14 to contact (e.g., slidably contact) each other to move and/or maintain the mandible into a forward position and/or to increase and/or maintain the interocclusal separation between the maxillary and mandibular dental arches. Angles within these ranges and/or having these values can therefore advantageously facilitate treating TMD by repositioning the jaw and/or by adjusting the bite. Angles within these ranges and/or having these values can also facilitate the reshaping of the airway into a more open configuration (e.g., from a less open first configuration to a more open second configuration). Each mandibular block 14 in a series can have the same or different maxillary guide surface angle 32 as one or more other mandibular blocks in the series.

FIG. 1 illustrates that the maxillary and mandibular guide surface angles 30, 32 of a maxillary and mandibular block pair (e.g., pair 12*a*-14*a*, pair 12*b*-14*b*) can be any two complementary or nearly complementary angles. For example, the first and second block pairs 12*a*-14*a* and 12*b*-14*b* can have angle pairs (listed as angle-angle, in degrees) of about 45-45, 40-50, 35-55, 30-60, 25-65, 20-70, 15-75, 10-80, 5-85, or vice versa—about 45-45, 50-40, 55-35, 60-30, 65-25, 70-20, 75-15, 80-10, 85-5. The maxillary blocks 12 can have the first listed complementary angle and the mandibular blocks 14 can have the second listed complementary angle in each of the angle-angle pairs. The mandibular blocks 14 can have the first listed complementary angle and the maxillary blocks 12 can have the second listed complementary angle in each of the angle-angle pairs. In this way, the maxillary and mandibular blocks 12, 14 can form cooperating pairs of blocks 12-14 and guide surfaces 26-28 as described above. However, the maxillary and mandibular guide surface angles 30, 32 can be non-complementary and still enable one or more portions of each of the guide surfaces 26, 28 to cooperate with one another. Moreover, the guide surfaces 26, 28 need not form surface angles 30, 32—which can occur where, for example, the guide surfaces are irregular, curved, polygonal, or any combination thereof, yet still advantageously be configured to interact and function as guide surfaces.

FIG. 1 illustrates that the maxillary first and second blocks 12*a*, 12*b* can have maxillary first and second guide surface angles 30*a*, 30*b*, respectively. The maxillary first and second guide surface angles 30*a*, 30*b* can be the same or different from one another. For example, the maxillary first guide surface angle 30*a* can be less than, equal to, or greater than the maxillary second guide surface angle 30*b*. The maxillary first guide surface angle 30*a* can be from about 1 degree to about 90 degrees greater or less than the maxillary second guide surface angle 30*b*, more narrowly from about 1 degree to about 45 degrees greater or less than the maxillary second guide surface angle 30*b*, more narrowly yet from about 1 degree to about 30 degrees greater or less than the maxillary second guide surface angle 30*b*, still more narrowly from about 1 degree to about 15 degrees greater or less than the maxillary second guide surface angle 30*b*, yet still more narrowly from about 1 degree to about 5 degrees greater or less than the maxillary second guide surface angle 30*b*, or vice versa.

FIG. 1 illustrates that the mandibular first and second blocks 14*a*, 14*b* can have mandibular first and second guide surface angles 32*a*, 32*b*, respectively. The mandibular first and second guide surface angles 32*a*, 32*b* can be the same or different from one another. For example, the mandibular first guide surface angle 32*a* can be less than, equal to, or greater than the mandibular second guide surface angle 32*b*. The mandibular first guide surface angle 32*a* can be from about 1 degree to about 90 degrees greater or less than the mandibular second guide surface angle 32*b*, more narrowly from about 1 degree to about 45 degrees greater or less than the mandibular second guide surface angle 32*b*, more narrowly yet from about 1 degree to about 30 degrees greater or less than the mandibular second guide surface angle 30*b*, still more narrowly from about 1 degree to about 15 degrees greater or less than the mandibular second guide surface angle 32*b*, yet still more narrowly from about 1 degree to about 5 degrees greater or less than the mandibular second guide surface angle 32*b*, or vice versa.

FIG. 1 illustrates that the maxillary guide surfaces 26 can extend away from an occlusal surface of the maxillary dentition and/or from a maxillary oral tray (not shown, e.g., a maxillary orthodontic tray), for example, toward the mandible. The mandibular guide surfaces 28 can extend away from an occlusal surface of the mandibular dentition and/or a mandibular oral tray (not shown, e.g., a mandibular orthodontic tray), for example, toward the maxilla. Each guide surface (e.g., guide surfaces 26, 28) can have a first end and a second end. The first and second ends can be the base of the guide surface and the second end can be the top of the guide surface. The base of the maxillary guide surface 26 can be closer to a surface of a maxillary tooth and/or maxillary oral tray than the top of the maxillary guide surface 26 and the base of the mandibular guide surface 28 can be closer to a surface of a mandibular tooth and/or mandibular oral tray than the top of the mandibular guide surface 28. For example, FIG. 1 illustrates that the bases of the maxillary and mandibular guide surfaces 26, 28 can be proximate to and extend from maxillary and mandibular occlusal surfaces, respectively, toward the opposing dentition; however, one or more of the bases can be offset from the occlusal surface or oral tray such that the offset base(s) are separated from the dentition or a surface of a maxillary or mandibular oral tray by about 0.5 mm to about 50 mm. The tops can be proximate to or separated from (e.g., by about 0.5 mm to about 50 mm) the opposing dentition. FIG. 1 illustrates that the tops of the mandibular guide surfaces 28 can be configured to be proximate the maxillary detention and/or oral tray and that the tops of the maxillary guide surfaces 26 can be configured to be separated from the mandibular dentition and/or oral tray.

The guide surfaces 26, 28 can extend along any portion of a length of a block, for example, 100% or less, 75% or less, 50% or less, 25% or less. For example, FIG. 1 illustrates that each guide surface 26, 28 can extend about 33% along a length of its respective block, thereby advantageously providing a large guide surface. Guide surfaces 26, 28 that extend along greater than about 10% of a length of a block can advantageously enable each block 12, 14 in a treatment series to be used for greater treatment period before a user graduates to the next block. Guide surfaces greater than this 10% threshold can reduce the number of blocks 12, 14 required in a treatment series. Guide surfaces greater than this 10% threshold can increase user comfort and tolerance for user error. Although not illustrated, each maxillary ramp 26 can extend about 100% along the length of a maxillary block 12, for example, from a maxillary block first end to a maxillary block second end such that the maxillary blocks 12 have a shape of a triangular wedge when viewed from the side. Similarly, each mandibular ramp 28 can extend about 100% along the length of a mandibular block 14, for example, from a mandibular block first end to a mandibular block second end such that the mandibular blocks 14 have a shape of a triangular wedge when viewed from the side.

FIG. 1 illustrates that the maxillary and mandibular guide surfaces 26, 28 can be sloped longitudinally such that the angles 30, 32 are the angles that are formed as the guide surfaces 26, 28 extend longitudinally across the blocks 12, 14, for example, from the anterior portion 20 to the posterior portion 22 of the blocks 12, 14. As a result, the guide surfaces 26, 28 can form one or more longitudinal slopes. Additionally or alternatively, the maxillary and mandibular guide surfaces 26, 28 can be sloped transversely such that the angles 30, 32 can be the angles that are formed as the maxillary guide surfaces 26 extend laterally across the block, for example, from a first lateral side to a second lateral side (e.g., left to right and/or right to left) of the blocks 12, 14, or from a longitudinal center to a first and/or second lateral side of the blocks 12, 14. As a result, the guide surfaces 26, 28 can form one or more transverse slopes. Each guide surface 26, 28 can have a longitudinal and/or transverse slope. The longitudinal and transverse guide surfaces can have the same or different slope from one another. For example, one or more guide surfaces can have a longitudinal slope of about 35 degrees and a transverse slope of about 20 degrees. The one or more longitudinal slopes can reposition the jaw and/or adjust the bite by advancing the mandible. The one or more transverse slopes can reshape the airway by causing palatal expansion, for example, by exerting an outward force on the dentition. Each block in a series can have the same or different longitudinal and/or transverse slope(s) as one or more other blocks in the series.

FIG. 1 illustrates the relative positions of the maxillary and mandibular blocks 12, 14 relative to the maxillary and mandibular dental arches, respectively. The maxillary blocks 12 (e.g., maxillary first and second blocks 12*a*, 12*b*) can be configured to overlay one or more posterior teeth and/or one or more anterior teeth. The maxillary blocks 12 can be configured to overlay a central incisor, a lateral incisor, a canine, one or more premolars, one or more molars, or any combination thereof. FIG. 1 illustrates that the maxillary first and second blocks 12*a*, 12*b* can overlay a portion of the posterior ends of the maxillary dental arch, for example, the second and third molars. The mandibular blocks 14 (e.g., mandibular first and second blocks 14*a*, 14*b*) can be configured to overlay one or more posterior teeth and/or one or more anterior teeth. The mandibular blocks 14 (e.g., mandibular first and second blocks 14*a*, 14*b*) can be configured to overlay a central incisor, a lateral incisor, a canine, one or more premolars, one or more molars, or any combination thereof. FIG. 1 illustrates that the mandibular first and second blocks 14*a*, 14*b* can overlay the posterior ends and an anterior portion of the mandibular dental arch, for example, the second premolar and the first, second and third molars. Each block in a series can have the same or different relative position as one or more other blocks in the series.

The location of the maxillary and/or mandibular blocks 12, 14 relative to a dentition and/or to each other can be determined by a dentist, orthodontist, one or more computer algorithms, or a combination thereof. For example, a computer program can be used to retrieve data from oral data acquisition devices (e.g., scanners, x-ray devices, cameras) to record and measure orthodontic malocclusions and teeth misalignments. A computer program can be used to retrieve data from oral data acquisition devices to record and measure the orthodontic correction of malocclusions and misalignments during treatment.

Figure 2:
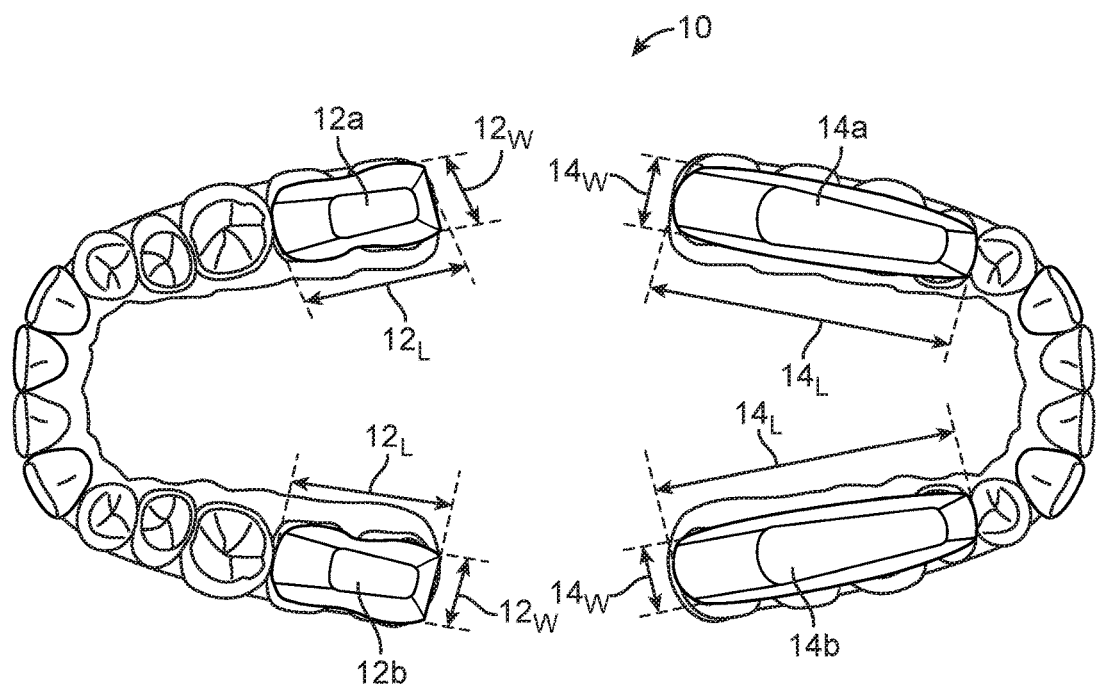
FIG. 2 illustrates a top elevational view of the oral appliance of FIG. 1.
Figure 3:
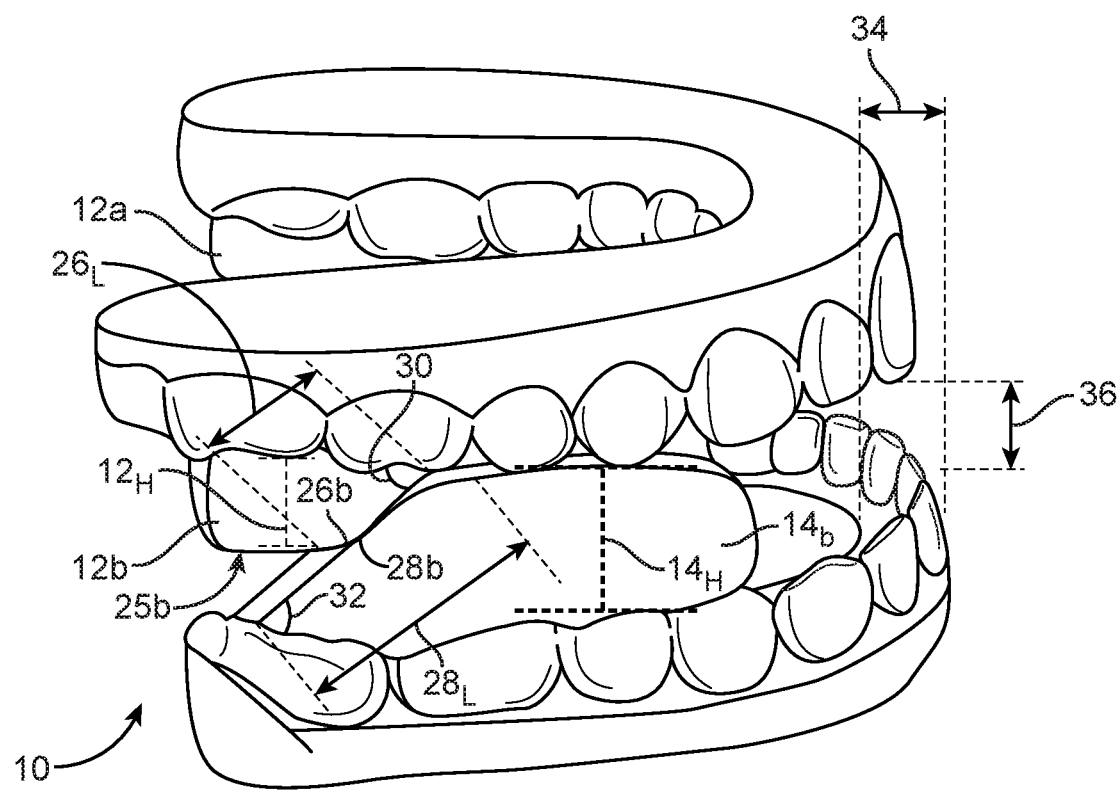
FIG. 3 illustrates a side isometric view of the oral appliance of FIG. 1 in a fully engaged and assembled configuration under compression.

FIGS. 2 and 3 illustrate that the maxillary blocks 12 (e.g., maxillary first and second blocks 12a, 12b) can each have a length $12_L$, a width $12_w$ and a height $12_H$. The length $12_L$ can be from about 1 mm to about 50 mm, including every 0.5 mm increment between about 1 mm and about 50 mm, for example, about 15.0 mm. The width $12_w$ can be from about 1 mm to about 30 mm, including every 0.5 mm increment between about 1 mm and about 30 mm, for example, 8.0 mm. The height $12_H$ can be from about 1 mm to about 50 mm, including every 0.5 mm increment between about 1 mm and about 50 mm, for example, 10.0 mm. Each maxillary block 12 in a series can have the same or different length $12_L$, width $12_w$, and/or height $12_H$ as one or more other maxillary blocks 12 in the series. The lengths $12_L$ of multiple or successive maxillary blocks 12 can each have the same length or one or more different lengths $12_L$. For example, the lengths $12_L$ of multiple or successive maxillary blocks 12 can become progressively longer, progressively shorter, follow another progressive pattern (e.g., increase and/or decrease), or remain constant. For example, the lengths $12_L$ of the maxillary blocks 12 in a series can increase from about 15.0 mm to about 20.0 mm, vice versa (e.g., decrease from about 15.0 mm to about 10.0 mm), increase from about 15.0 to about 18.0 mm and then decrease to about 16.5 mm, or remain constant at about 15.0 mm. The widths $12_w$ of multiple or successive maxillary blocks 12 can each have the same width or one or more different widths $12_w$. For example, the widths $12_w$ of multiple or successive maxillary blocks 12 can become progressively longer, progressively shorter, follow another progressive pattern (e.g., increase and/or decrease), or remain constant. For example, the widths $12_w$ of the maxillary blocks 12 in a series can increase from about 8.0 mm to about 13.0 mm, vice versa (e.g., decrease from about 8.0 mm to about 3.0 mm), increase from about 8.0 to about 11.0 mm and then decrease to about 10.0 mm, or remain constant at about 8.0 mm. The heights $12_H$ of multiple or successive maxillary blocks 12 can each have the same height or one or more different heights $12_H$. The height $12_H$ can be a maximum height. For example, the heights $12_H$ of multiple or successive maxillary blocks 12 can become progressively longer, progressively shorter, follow another progressive pattern (e.g., increase and/or decrease), or remain constant. For example, the heights $12_H$ of the maxillary blocks 12 in a series can increase from about 10.0 mm to about 15.0 mm, vice versa (e.g., decrease from about 15.0 mm to about 10.0 mm), increase from about 8.0 to about 11.0 mm and then decrease to about 10.0 mm, or remain constant at about 10.0 mm.

FIGS. 2 and 3 illustrate that the mandibular blocks 14 (e.g., mandibular first and second blocks 14a, 14b) can each have a length $14_L$, a width $14_w$ and a height $14_H$. The length $14_L$ can be from about 1 mm to about 50 mm, including every 0.5 mm increment between about 1 mm and about 50 mm, for example, about 35.0 mm. The width $14_w$ can be from about 1 mm to about 30 mm, including every 0.5 mm increment between about 1 mm and about 30 mm, for example, 8.0 mm. The height $12_H$ can be from about 1 mm to about 50 mm, including every 0.5 mm increment between about 1 mm and about 50 mm, for example, 3.0 mm. Each mandibular block 14 in a series can have the same or different length $14_L$, width $14_w$, and/or height $14_H$ as one or more other mandibular blocks 14 in the series. The lengths $14_L$ of multiple or successive mandibular blocks 14 can each have the same length or one or more different lengths $14_L$. For example, the lengths $14_L$ of multiple or successive mandibular blocks 14 can become progressively longer, progressively shorter, follow another progressive pattern (e.g., increase and/or decrease), or remain constant. For example, the lengths $14_L$ of the mandibular blocks 14 in a series can increase from about 35.0 mm to about 40.0 mm, vice versa (e.g., decrease from about 35.0 mm to about 30.0 mm), increase from about 35.0 to about 38.0 mm and then decrease to about 36.5 mm, or remain constant at about 35.0 mm. The widths $14_w$ of multiple or successive mandibular blocks 14 can each have the same width or one or more different widths $14_w$. For example, the widths $14_w$ of multiple or successive mandibular blocks 14 can become progressively longer, progressively shorter, follow another progressive pattern (e.g., increase and/or decrease), or remain constant. For example, the widths $14_w$ of the mandibular blocks 14 in a series can increase from about 8.0 mm to about 13.0 mm, vice versa (e.g., decrease from about 8.0 mm to about 3.0 mm), increase from about 8.0 mm to about 11.0 mm and then decrease to about 10.0 mm, or remain constant at about 8.0 mm. The heights $14_H$ of multiple or successive mandibular blocks 14 can each have the same height or one or more different heights $14_H$. The height $14_H$ can be a maximum height. For example, the heights $14_H$ of multiple or successive mandibular blocks 14 can become progressively longer, progressively shorter, follow another progressive pattern (e.g., increase and/or decrease), or remain constant. For example, the heights $14_H$ of the mandibular blocks 14 in a series can increase from about 3.0 mm to about 8.0 mm, vice versa (e.g., decrease from about 3.0 mm to about 0.5 mm), increase from about 3.0 mm to about 6.0 mm and then decrease to about 4.5.0 mm, or remain constant at about 3.0 mm.

The length $12_L$ can be greater than, equal to, or less than the length $14_L$. For example, FIG. 2 illustrates that the length $12_L$ can be less than the length $14_L$. The width $12_w$ can be greater than, equal to, or less than the width $14_w$. For example, FIG. 2 illustrates that the width $12_w$ can be about equal to the width $14_w$. The height $12_H$ can be greater than, equal to, or less than the height $14_H$. For example, FIG. 2 illustrates that the height $12_H$ can be less than the height $14_H$. Each block 12, 14 can have one or more lengths, widths, heights, or any combination thereof.

FIG. 3 illustrates that the guide surfaces 26 (e.g., guide surface 26b) can have a guide surface length $26_L$ and that the guide surfaces 28 (e.g., guide surface 28b) can have a guide surface length $28_L$. The surface length $26_L$ can be from about 1 mm to about 50 mm, including every 0.5 mm increment between about 1 mm and about 50 mm, for example, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm. The surface length $28_L$ can be from about 1 mm to about 50 mm, including every 0.5 mm increment between about 1 mm and about 50 mm, for example, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm. Each block in a series can have the same or different guide surface length $26_L$ as one or more other blocks in the series. The guide surface lengths $26_L$ of multiple or successive maxillary blocks 12 can each have the same length or one or more different lengths $26_L$. For example, the guide surface lengths $26_L$ of multiple or successive maxillary blocks 12 can become progressively longer, progressively shorter, follow another progressive pattern (e.g., increase and/or decrease), or remain constant. For example, the guide surface lengths $26_L$ of the maxillary blocks 12 in a series can increase from about 10.0 mm to about 20.0 mm, vice versa (e.g., decrease from about 10.0 mm to about 5.0 mm), increase from about 10.0 to about 13.0 mm and then decrease to about 5.0 mm, or remain constant at about 10.0 mm. The guide surface lengths $28_L$ of multiple or successive mandibular blocks 14 can each have the same length or one or more different lengths $28_L$. For example, the guide surface lengths $28_L$ of multiple or successive mandibular blocks 12 can become progressively longer, progressively shorter, follow another progressive pattern (e.g., increase and/or decrease), or remain constant. For example, the guide surface lengths $26_L$ of the mandibular blocks 12 in a series can increase from about 10.0 mm to about 20.0 mm, vice versa (e.g., decrease from about 10.0 mm to about 5.0 mm), increase from about 10.0 to about 13.0 mm and then decrease to about 5.0 mm, or remain constant at about 10.0 mm.

FIG. 3 illustrates that one or more of the maxillary and mandibular blocks 12, 14 can have a free surface 25 (also referred to as a hanging surface) positioned opposite a tooth surface 24 (e.g., tooth surface 24a and/or 24b) that is configured to not contact an opposing block (e.g., any surface of the opposing block), an opposing dental or orthodontic tray, an opposing dentition, or any combination thereof. For example, FIG. 1 illustrates that one or more maxillary blocks 12 can have a free surface 25. The maxillary first block 12a can have a maxillary first block hanging surface 25a and/or the maxillary second block 12b can have a maxillary second block hanging surface 25b. A hanging surface 25 can advantageously provide more space for the tongue in the oral cavity, increase the size of the airway and help keep open the airway. Additionally or alternatively, a hanging surface can advantageously inhibit or prevent the blocks 12, 14 from triggering a person's gag reflex, for example, by reducing the size of the oral appliance 10 positioned in the back of the oral cavity.

FIG. 3 illustrates that a gap can form between a free hanging surface 25 (e.g., the maxillary second block hanging surface 25b) and an opposing dentition (e.g., the mandibular dentition). The gap can be from about 0 mm to about 50 mm, more narrowly from about 1 mm to about 20 mm, yet more narrowly from about 1 mm to about 15 mm, yet still more narrowly from about 1 mm to about 10 mm, including every 0.5 mm increment within these ranges, for example, about 5 mm, about 6 mm, about 7 mm, about 8 mm, about 9 mm, about 10 mm. The gap can be the shortest distance between the free surface 25 and the opposing dental tray, orthodontic tray, or teeth. The gap can be the greatest distance between the free surface 25 and the opposing dental tray, orthodontic tray, or teeth. The gap can be measured between any point on an opposing dental tray, orthodontic tray, or teeth to any point on the hanging surface 25. The point on the hanging surface may or may not correspond with a point that is closest to or farthest from the opposing dental tray, orthodontic tray, or teeth.

FIG. 3 illustrates a variation of the relative positions of the maxillary and mandibular blocks 12, 14 to one another when the jaw is in a closed position. FIG. 3 illustrates that when the jaw is fully closed at least a portion of a posterior portion 22 of the maxillary blocks 12 (e.g., the maxillary first and second blocks 12a, 12b) can be posterior to at least a portion of a posterior portion 22 of the mandibular blocks 14 (e.g., the mandibular first and second blocks 14a, 14b), or vice versa (if, for example, the positions of the blocks 12, 14 are reversed such that the maxillary blocks 12 are placed in their same relative positions on the mandibular dental arch and the mandibular blocks 14 are place in their same relative positions on the maxillary dental arch). For example, FIG. 3 illustrates that the maxillary blocks 12 do not extend anterior to the top of the ramp of the mandibular blocks 14, and are accordingly posterior to the remaining portion of the mandibular blocks 14.

The dimensions and relative positions of the blocks 12, 14 disclosed herein will depend on, and can be customized to accommodate, for example, a person's airway, dental and/or orthodontic needs, their anatomy, the number of blocks in a series, the number oral trays in a series, or any combination thereof; thus, although various positions, ranges and values are disclosed, each permutation of the disclosed positions, ranges and values and equivalents thereof is considered critical to the overall design of the oral appliance 10, as each combination of dimensions and positions, when used together to reposition the jaw, adjust the bite, and/or reshape and/or maintain a person's airway, is critical to providing the treatment desired. Additionally, each block in a series can have any combination of the dimensions and positions disclosed, as the design of each block in a series will depend on a person's unique dentition and other craniofacial structures as well as the implemented orthodontic, TMD, and/or SBD treatment plan. If the foregoing disclosure yet lacks clarity, every permutation of block dimensions and positions within the ranges and values disclosed is hereby explicitly disclosed, for example, in 0.1 mm increments, such that any combination of block dimensions and/or relative positions is claimable.

The first and second maxillary blocks 12a, 12b can be connected via one or more maxillary connectors. The maxillary connector(s) can be a wire, resilient wire, polymer strand, resilient polymer strand, dental tray, orthodontic tray, or any combination thereof that conform to, extend along, or wrap around a buccal side, a lingual side, and/or an occlusal surface of at least a portion of the maxillary dental arch. A first end of the maxillary connector(s) can be attached to or integrated with any portion of the maxillary first or second block 12a, 12b and a second end of the maxillary connector(s) can be attached to or integrated with any portion of the other of the maxillary first or second block 12a, 12b. The maxillary connector(s) can be used to stabilize the first and second maxillary blocks 12a, 12b. The maxillary connector(s) can be designed and/or manipulated (e.g., progressively manipulated over a series of treatments) to orthodontically move maxillary teeth. The first and second mandibular blocks 14a, 14b can be connected via one or more mandibular connectors. The mandibular connector(s) can be a wire, resilient wire, polymer strand, resilient polymer strand, dental tray, orthodontic tray, or any combination thereof that conform to, extend along, or wrap around a buccal side, a lingual side and/or an occlusal surface of at least a portion of the mandibular dental arch. A first end of the mandibular connector(s) can be attached to or integrated with any portion of the mandibular first or second block 14a, 14b and a second end of the mandibular connector(s) can be attached to or integrated with any portion of the other of the mandibular first or second block 14a, 14b. The mandibular connector(s) can be used to stabilize the first and second mandibular blocks 14a, 14b. The mandibular connector(s) can be designed and/or manipulated (e.g., progressively manipulated over a series of treatments) to orthodontically move mandibular teeth. Orthodontic and dental trays are individually and collectively referred to throughout as oral trays such that an oral tray can be an orthodontic and/or a dental tray, for example, an aligner (also referred to as an orthodontic tray), a whitening tray, or an orthodontic teeth whitening aligner that is configured to move and whiten at least one tooth. Oral trays are also referred to as aligners and aligner components throughout.

The blocks 12, 14 can be attached to or integrated with a maxillary and/or mandibular oral tray. For example, the maxillary blocks 12 can be integrated with a maxillary and/or mandibular oral tray and/or the mandibular blocks 14 can be integrated with a maxillary and/or mandibular oral tray. A series of oral trays can be designed to progressively reposition the maxillary and/or mandibular teeth in two or more successive steps, for example, as disclosed in PCT Publication WO 2016/004415 and U.S. application Ser. No. 15/386,280 (published as US 2017/0100214), both of which have been incorporated herein by reference in their entireties for all purposes. Each oral tray in a series can have a tooth surface that has a geometry that corresponds to an intermediate or end tooth arrangement intended for the oral tray in the series. The oral trays can be sufficiently resilient to accommodate or conform to misaligned teeth, but apply sufficient force against the misaligned teeth to reposition the teeth to the intermediate or end arrangement as desired for the particular treatment step. A series of oral trays can have geometries selected to progressively reposition teeth from a first arrangement through one or more successive intermediate arrangements to a final arrangement. A series of trays can have 1 to 100 maxillary trays and 1 to 100 mandibular trays, for example, 1 to 55 maxillary trays and 1 to 55 mandibular trays, 1 to 50 maxillary trays and 1 to 50 mandibular trays, 1 to 45 maxillary trays and 1 to 45 mandibular trays, 1 to 40 maxillary trays and 1 to 40 mandibular trays, less than 40 maxillary trays 12 and less than 40 mandibular trays, including every 1 tray increment within these ranges, or any combination thereof. For example, a series of trays can have 40, 41, 42, 43, 44, 45, 46, 47, 48, 49, or 50 maxillary trays and 40, 41, 42, 43, 44, 45, 46, 47, 48, 49, or 50 mandibular trays. The number of maxillary trays can be the same or different as the number mandibular trays in a series. The trays can orthodontically move the teeth into one or more correct physiological position. For example, the trays can orthodontically move the teeth into one or more positions that are physiologically correct for the TMJ and musculature at the same time as TMD treatment with a TMD appliance.

Each tray in a series can be configured to move one or more teeth, or one or more trays in a series can be configured to not move any teeth. For example, where the mandibular teeth are in a desired alignment but the position of the maxillary teeth are still in need of an adjustment, the mandibular tray can be configured to maintain the position of the mandibular teeth and the maxillary tray can be configured to move one or more maxillary teeth. Further, one or multiple dimensions of the TMD aspect of the oral appliance 10, for example the TMD craniofacial adjustment blocks 12 and 14 shown in FIGS. 1-3, can be progressively adjusted in a series of oral appliances 10 to progressively reposition the jaw to alleviate and eliminate TMD, or alleviate or eliminate one or more symptoms thereof. Each TMD component in a series can have an arrangement or geometry that corresponds to an intermediate or end jaw position intended for the TMD component in the series. The TMD components can be sufficiently resilient to reposition the mandible to the intermediate or end arrangement as desired for the particular treatment step. A series of TMD components can have geometries selected to progressively reposition the mandible from a first position through one or more successive intermediate positions to a final position. In this way, the aligner component and/or the TMD component of the oral appliance 10 can concurrently and progressively orthodontically move teeth and treat TMD, for example, by progressively adjusting the jaw position with each oral appliance 10 in a series. The number of oral appliances 10 in a series can be the same as that described herein with respect to the number of oral trays in a series (e.g., as described earlier in this paragraph).

The number of steps in a series for the aligner components to move one or more teeth from an initial arrangement to a final arrangement can be the same or different than the number of steps in a series for the TMD components to move the jaw from an initial position to a final position. As a result, some aligner components (e.g., 1 to $N_A$–1 aligner components, where $N_A$ is the total number of aligner components in a series) may not have a geometry configured to move one or more teeth, instead having a geometry to maintain the position of one or more teeth while the corresponding TMD component in the series can be configured to progressively move the jaw to a new position (e.g., an intermediate or a final position). Also, some TMD components (e.g., 1 to $N_T$–1 TMD components, where $N_T$ is the total number of TMD components in a series) may not have an arrangement or geometry configured to move the jaw, instead having an arrangement or geometry to maintain the position of the jaw while the corresponding aligner component in the series has a geometry configured to progressively move one or more teeth. The total number of aligner and TMD components $N_A$, $N_T$ can be the same or different from each, for example, $N_A$ and $N_T$ can each be the same as the number of oral appliances 10 in a series, and $N_A$ can be greater than, equal to, or less than $N_T$ as described above. In this way, the number of steps in a series for both the aligner and TMD components can be the same number as the number of oral appliances 10 in the series, or a lesser number, or can be the same number as the number of aligner and TMD components in a series, respectively, or a lesser number. As a result, the number of treatment steps for both the aligner and TMD components can be the same or fewer than the number of components in a series of appliances 10.

The blocks 12, 14 can be modular such that they can be removably attached to a maxillary and/or mandibular oral tray, for example, to an orthodontic tray and/or to a dental tray (i.e., any tray without an orthodontic function). The blocks 12, 14 can be attached to one or multiple oral trays with one or multiple attachment mechanisms (also referred to as anchors), such as clasps, clips, hooks, elastic hooks, barbs, spurs, fasteners, or any combination thereof. Additionally or alternatively, the blocks 12, 14 can fit over a portion of an oral tray with a friction fit and/or a snap fit. For example, the oral tray can have a ridge over which the blocks 12, 14 can be snapped. The ridge can extend at least partially along a surface of the oral tray. A first end (e.g., a base) of each maxillary block 12 can be anchored to a maxillary oral tray. A second end (e.g., a top portion) of each maxillary block 12 can be anchored to a mandibular oral tray. A first end (e.g., a base) of each mandibular block 14 can be anchored to a mandibular oral tray. A second end (e.g., a top portion) of each mandibular block 14 can be anchored to a maxillary oral tray. A modular block design can be especially advantageous where a series of orthodontic trays are designed as disclosed in WO 2016/004415, as the modular design can allow the reuse and/or repositioning of the blocks 12, 14 along the arch of the maxillary and/or mandibular dentition on a single aligner or on multiple successive aligners. The modular design can advantageously allow the repositioning of one or more blocks 12, 14 from a first position on an oral tray to one or more other positions on the oral tray different from the first position. For example, the modular design can allow the repositioning each block (e.g., blocks 12 and/or 14) in a series 1 to 100 times on one or multiple oral trays, including every increment of 1 between 1 and 100. A modular design can also advantageously allow a series of blocks to be mixed and matched with each oral tray in an oral tray series.

One or both guide surfaces of a guide surfaces pair 26-28 (e.g., pair 26a-28a and/or pair 26b-28b) can have a coating or otherwise comprise a material which permits relative motion between two opposed guide surfaces in a first direction and resists relative motion between two opposed guide surfaces in a second direction opposite the first direction. For example, the mandibular blocks 14 can be configured to engage the maxillary blocks 12 and slide forward along the guide surfaces 26 of the maxillary blocks 12 upon the application of a compressive force between two opposing maxillary and mandibular blocks 12, 14 (e.g., upon closing the jaw from an open position or by otherwise "biting down" on the blocks 12, 14). As another example, the mandibular blocks 14 can be configured to engage the maxillary blocks 12 and slide forward along the guide surfaces 26 of the maxillary blocks 12 in a first direction when the jaw relaxes or is voluntarily opened and then relaxed and be prevented or inhibited from sliding along the guide surfaces 26 in a second direction opposite the first direction. The guide surfaces (e.g., guide surfaces 26 and/or 28) can have a first coefficient of friction associated with movement of the mandibular blocks 12 in a first direction and a second coefficient of friction associated with movement of the mandibular blocks 12 in a second direction opposite the first direction. The second coefficient of friction can be greater than the first coefficient of friction. The first and second coefficients of friction can be static coefficients of friction $\mu_s$. The first and second coefficients of friction can be kinetic coefficients of friction $\mu_k$.

One or both guide surfaces of a guide surface pair 26-28 (e.g., pair 26a-28a and/or pair 26b-28b) can have a coating or otherwise comprise a material (e.g., an adhesive or a ferromagnetic material) which inhibits relative motion between two opposed guide surfaces when they interact. Additionally or alternatively, one or more magnets can be placed in the blocks 12, 13 such that the maxillary blocks 12 magnetically attract the mandibular blocks 14 and vice versa.

The maxillary and mandibular blocks 12, 14 can comprise a thermoplastic material. The maxillary and mandibular blocks 12, 14 can be thermoformed with the aid of a computer algorithm. The maxillary and mandibular aligners can comprise a thermoplastic material. The maxillary and mandibular aligners can be thermoformed with the aid of a computer program. The maxillary blocks 12 and the maxillary aligners can be attached to, integrated with, or monolithically formed with one another. The mandibular blocks 14 and the mandibular aligners can be attached to, integrated with, or monolithically formed with one another.

The maxillary and mandibular blocks 12, 14 can be rigid such that they resist deformation under pressure or semi-rigid such that they permit deformation and/or are compliant under pressure. Semi-rigid and/or compliant materials can advantageously increase user comfort and prevent, inhibit, or limit TMD, for example, sleep bruxism.

The blocks 12, 14 can be solid or hollow. For example, the blocks 12, 14 can have one or more airway channels (e.g., 1 to 10 or more airway channels). The airway channels can extend at least partially laterally and/or at least partially longitudinally through the blocks 12, 14. The airway channels can extend through the blocks 12, 14 from the buccal side 16 to the lingual side 18. The airway channels can extend through the blocks 12, 14 from an anterior side to a posterior side. One or more of the airway channels of a maxillary block 12 can be at least partially aligned (e.g., partially or completely collinear) with one or more channels of a mandibular block 14. Each channel can have an anterior end and a posterior end. A posterior end of the channel of an anterior block (e.g., the mandibular blocks 14 in FIG. 1) can overlap completely or partially with an anterior end of the channel of a posterior block (e.g., the maxillary blocks 12 in FIG. 1). The posterior ends of the airway channels of the posterior blocks (e.g., the maxillary blocks 12 in FIG. 1) can be directed toward the pharynx to facilitate inhalation and exhalation. A posterior portion of the airway channels in the posterior blocks (e.g., the maxillary blocks 12 in FIG. 1) can be curved such that the posterior ends of the posterior blocks are directed toward the pharynx or the base of the tongue. The airway channels can be straight, curved, tapered, or any combination thereof.

A cooperating pair of blocks 12-14 can have 1 to 10 or more airway channels. For example, the cooperating pair of blocks 12a-14a and 12b-14b can each have one maxillary airway channel and two mandibular airway channels extending at least partially longitudinally and/or laterally through the blocks 12a, 12b, 14a, 14b. One of the mandibular airway channels can be at least partially aligned with the maxillary airway channel. The three airway channels (the one maxillary and two mandibular channels) can thereby advantageously form two airway channels from an anterior portion of the oral appliance 10 to a posterior portion of the oral appliance 10. The one or more airway channels in the oral appliance 10 can decrease the amount of dead space in the oral cavity by increasing the size of the oral cavity available for airflow through the oral cavity by allowing air to flow through the blocks 12, 14. By increasing the volume in the oral cavity available for airflow, the one or more airway channels can advantageously reduce the amount of respiratory effort required for inhalation and exhalation and/or decrease the velocity of the air passing through oral cavity, and can therefore, in turn, prevent, inhibit, and/or reduce the likelihood of an SBD event and/or the occurrence of snoring while using the TMD appliance 10. The one or more airway channels can and/or can help prevent, inhibit, and/or reduce SBD and/or snoring.

The airway channels can be substantially the same size as the block or any lesser size, collectively or individually. For example, a transverse and/or longitudinal cross-sectional area of the airway channels can be about 1% to about 100% of a transverse and/or longitudinal cross-sectional area of the blocks 12, 14, more narrowly from about 1% to about 95%, more narrowly still from about 1% to about 90%, including every 1% increment within these ranges, for example, about 25%, 50%, 75%, 90%, or 95%. A length of the airway channels can be about 1% to about 100% of a length of the blocks 12, 14, more narrowly from about 1% to about 90%, more narrowly still from about 1% to about 80%, including every 1% increment within these ranges, for example, about 25%, 50%, 75%, or 95%. The airway channels can extend laterally across the blocks 12, 14 such that the airway channels extend across about 1% to about 100% the width of a block, more narrowly from about 1% to about 90%, more narrowly still from about 1% to about 80%, including every 1% increment within these ranges, for example, about 25%, 50%, 75%, or 95%.

One or more sensors can be positioned in one or multiple airway channels, integrated into a wall of one or multiple airway channels, integrated or positioned on an outer surface of one or multiple blocks 12, 14, integrated in one or multiple blocks 12, 14, integrated or positioned on one or more oral trays, or any combination thereof. The one or more sensors can be flow sensors, pressure sensors, temperature sensors, or any combination thereof. The sensor(s) can be in communication with a controller configured to activate an alarm when an obstruction is detected, for example, when a flow sensor detects a stoppage or reduction in flow that exceeds a time interval threshold, when a pressure sensor detects a drop in pressure that exceeds a pressure drop threshold, when a temperature sensor detects a temperature increase of exhaled or oral cavity air that exceeds a temperature threshold, or any combination thereof. The alarm can be auditory and/or tactile (e.g., vibration), and can be emitted from an alarm mechanism, including, for example, the controller. The controller can be integrated with the TMD device 10 or be in wireless communication therewith. The controller can be configured to communicate an alarm signal to a smartphone or other computing device which can process the signal and emit an auditory and/or tactile alarm. The alarm can be configured to wake a person up from a potentially dangerous SBD event. One or more sensors (e.g., one or more pressure sensors) can be in communication with the controller to detect whether the oral appliance 10 is properly or improperly positioned. The controller can be configured to activate an alarm if the oral appliance 10 is improperly positioned, for example, if it becomes dislodged when a person is sleeping (e.g., if one or more pressure sensors detect a pressure drop that exceeds a pressure drop threshold).

Figure 4C:
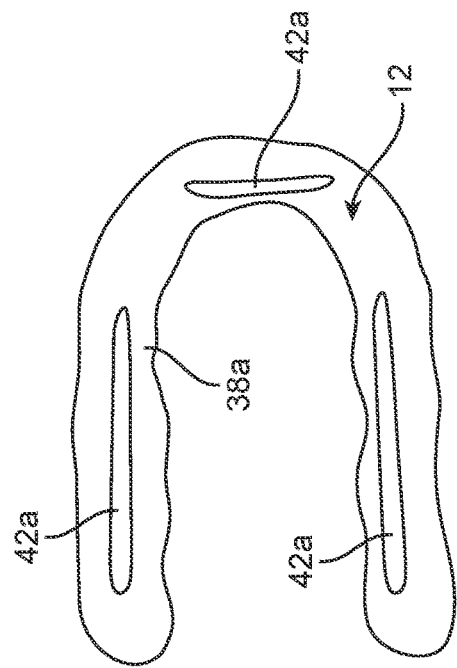
FIGS. 4a, 4b, and 4c illustrate a schematic of a variation of locking mechanisms of an oral appliance.
Figure 4B:
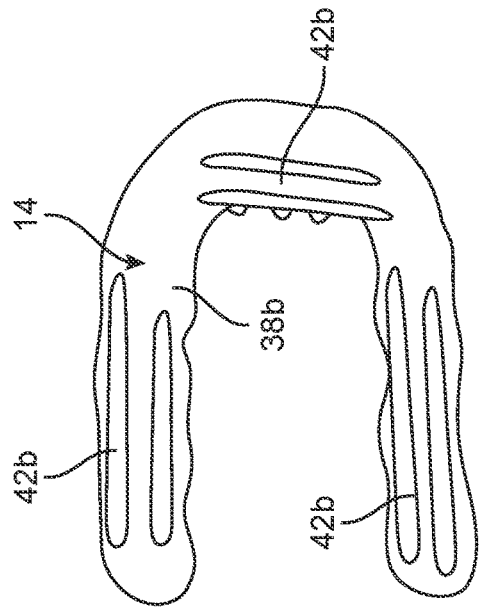
Figure 4A:
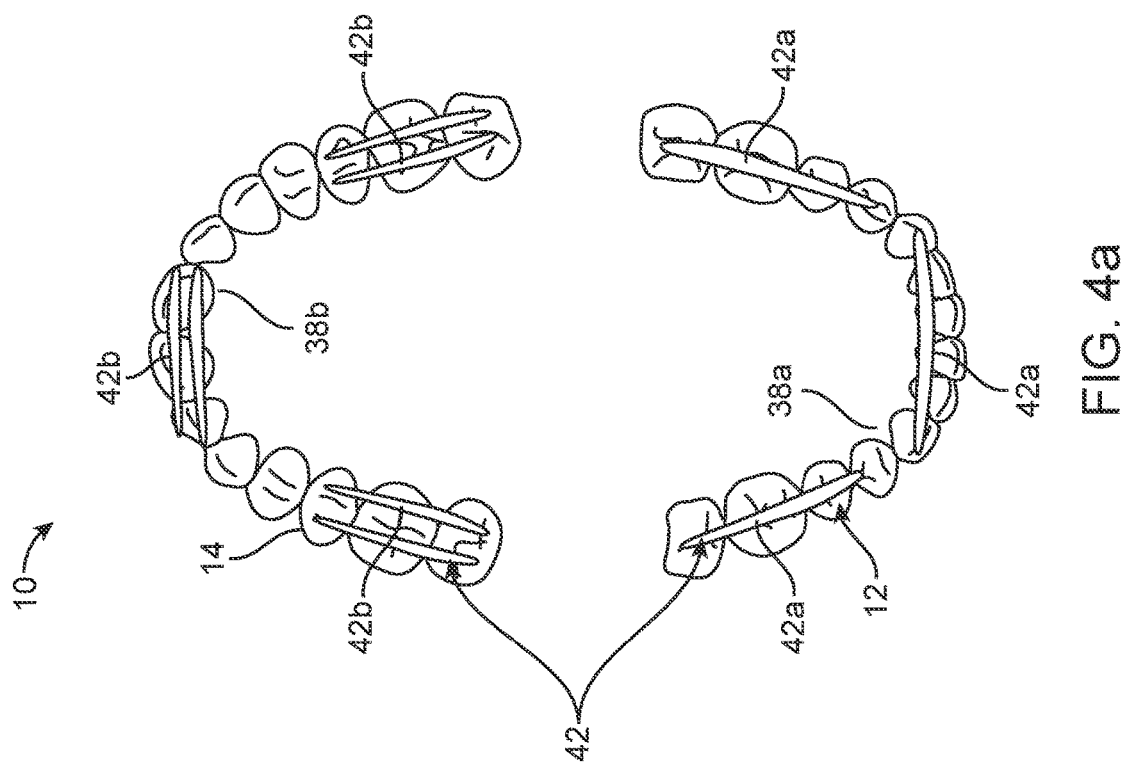

FIGS. 4a, 4b, and 4c illustrate that the appliance 10 can have attachable or interlockable maxillary and mandibular aligners, which can friction-fit, screw-fit, snap-fit, or otherwise couple to each other and lock the appliance 10 in a treatment position. TMD treatment can lock the jaw into position, for example, into an intermediate or final position in each of the corresponding steps of a treatment series. For example, FIGS. 4a, 4b, and 4c illustrate that the appliance 10 can have one or more locking mechanisms 42 that can lock the jaw into position (e.g., into a TMD treatment position, for example, one or more desired intermediate positions, or the final desired position). For example, the appliance 10 can have one or more maxillary locking mechanisms 42a and/or one or more mandibular locking mechanisms 42b. For example, the appliance 10 can have 1 to 5 maxillary locking mechanisms 42a and/or 1 to 5 mandibular locking mechanisms 42b. The number of maxillary locking mechanisms 42a can be less than, equal to, or greater than the number of mandibular locking mechanisms 42b. For example, FIGS. 4a, 4b, and 4c illustrate that the appliance 10 can have three maxillary locking mechanisms 42a and three mandibular locking mechanisms 42b.

The maxillary and mandibular aligners 38a, 38b, each of which can have one or more TMD devices or components attached or integrated therewith, can be attached to (e.g., interlockable with) one another, for example, via the one or more locking mechanisms 42. The locking mechanisms 42 can interlock with one another such that the maxillary aligner 38a can be attached to the mandibular aligner 38b. The locking mechanisms 42 can interlock with an aligner 38 and/or to the TMD aspect of the appliance 10. The locking mechanisms 42 can be attached to the aligners 38 (e.g., maxillary aligner 38a and/or mandibular aligner 38b) and/or to one or more TMD devices or components of the appliance 10.

The locking mechanisms 42 can have an unlocked configuration and one or more locked configurations (e.g., 1, 2, 3, 4, or 5 or more locked configurations). For example, the locking mechanisms 42 can have first, second, third, fourth, and/or fifth locked configurations that can be sequentially lockable (e.g., with the first configuration lockable first and the fifth configuration lockable last). Each locked configuration can permit or restrict a different amount of movement relative to another locked configuration, including a complete constraint on movement relative to the locked configuration. Each locked configuration can permit or restrict the same amount of movement relative to the other locked configurations, including a complete constraint on movement relative to the locked configuration. Each locked configuration can lock the maxillary and mandibular together a different distance apart. For example, the first, second, third, fourth, and fifth locked configurations can lock the maxillary and mandibular aligners (e.g., aligners 38a and 38b) from about 1 mm to about 5 mm, from about 6 mm to about 10 mm, from about 11 mm to about 15 mm, from about 16 mm to about 20 mm, and from about 21 mm to about 25 mm, respectively, or vice versa. The multiple locked configurations can each correspond to a different treatment step for a TMD component such that the number of lockable configurations corresponds to a number of sub-treatment steps for each TMD component in each step of a series of oral appliances 10.

When in a locked configuration, the locking mechanisms 42 can prevent the jaw from moving (e.g., opening or closing vertically or moving from side to side) and/or can limit the amount by which the lower jaw is able to move, for example, by preventing or limiting the amount of relative movement between the aligners 38 and/or between one or more aspects of the TMD devices or components of the appliance 10. For example, when the locking mechanisms 42 are engaged and the appliance 10 is in a locked configuration, the locking mechanisms 42 can prevent all movement of the lower jaw (e.g., by preventing all relative movement between the aligners 38). As another example, when the locking mechanisms 42 are engaged and the appliance 10 is in a locked configuration, the locking mechanisms 42 can allow the lower jaw to have one, two, three, four, five, or six degrees of freedom such that the lower jaw is translatable along and/or rotatable about one, two, and/or three axes (e.g., along and/or about one, two, and/or three mutually perpendicular axes such as x, y, and/or z Cartesian axes). To permit the lower jaw to move, the locking mechanisms 42 can permit relative movement between the aligners 38 and/or between one or more aspects of the TMD devices or components of the appliance 10. For example, when in a locked configuration, the locking mechanisms 42 can permit the lower jaw to translate from about 0.5 mm to about 5 mm, including every 0.5 mm increment within this range, for example, about 2.0 mm, along one, two, or three axes. For example, when in a locked configuration, the locking mechanisms can permit the lower jaw to rotate from about 1 degree to about 30 degrees, including every 1 degree increment within this range, for example, about 10 degrees, about one, two, or three axes. When in a locked configuration, the locking mechanisms 42 can be in a neutral, or "zero," position, and translation and/or rotation of the jaw can be measured relative to this neutral position. For example, movement of the mandibular aligner 38b can be measured relative to the TMD aspect of the appliance 10 and/or relative to the maxillary aligner 38a such that the translational and angular ranges described above refer to the displacements of the mandibular aligner 38b that are permitted when the locking mechanisms 42 are in a locked configuration and the lower jaw moves.

The locking mechanisms 42 can impart a restorative force to the lower jaw to return to the neutral position once displaced (e.g., translated and/or rotated) away from the neutral position. Additionally or alternatively, the locking mechanisms 42 can include one or more elastic bands and/or guide surfaces apart from the locking mechanisms 42 to impart a restorative force or otherwise encourage a return to the neutral position.

The locking mechanisms 42 can be tethers clasps, clips, hooks, elastic hooks, barbs, spurs, fasteners, elastic bands, interlocking male and female components, or any combination thereof. The elastic bands can wrap around one or more hooks attached to or integrated with the appliance 10. For example, FIGS. 4a, 4b, and 4c illustrates that the maxillary locking mechanisms 42a can each be a male component that can fit into or otherwise lock with a corresponding mandibular locking mechanism 42b, where each mandibular locking mechanism 42b can have a female receptor configured to receive the male maxillary locking mechanisms 42a.

The male and female locking mechanisms 42a and 42b can position/lock the lower jaw in a desired position (e.g., an improved or correct position) while the teeth are moving orthodontically, or while an orthodontic force is being exerted on the teeth to move them orthodontically. The male locking mechanisms 42a can have a protrusion (e.g., a ridge) that fits into a groove or slot of the female locking mechanisms 42a. The locking mechanisms can be on the maxillary and mandibular guide surfaces 26, 28.

The male component can be a protrusion and the female component can be a recess, a groove, or a hole. The male component can have a form factor that is slightly larger than the female component to generate an interference fit. For example, the protrusion can have a form factor that is slightly larger than the recess, hole, or groove such that an interference fit is produced when the protrusion is inserted into the recess, hole, or groove. The male component can have a form factor that is slightly smaller than the female component to generate an interference fit. For example, the protrusion can have a form factor that is slightly smaller than the recess, hole, or groove such that an interference fit is produced when the protrusion is inserted into the recess, hole, or groove. A maxillary block 12a can be attached to a mandibular block 12b and/or to a mandibular aligner 38b via the locking mechanism 42 (e.g., 42a and/or 42b). A maxillary aligner 38a can be attached to a mandibular block 12b and/or to a mandibular aligner 38b via the locking mechanisms (e.g., 42a and/or 42b).

Different blocks 12 and/or aligners 38 in a series can have different degrees of freedom when in an attached configuration. Changing the motion permitted by the jaw during treatment with different appliances 10 in the series can desirably prevent or inhibit the user from developing new TMD symptoms and/or allow the TMD device 10 to treat TMD. The appliances 10 in the series can restrict movement of the lower jaw differently than one or more preceding appliances 10 and/or differently than one or more subsequent appliances 10. The amount of movement or the degrees of freedom can be changed for every appliance 10 in the series, or every 2-50 appliances 10 in the series, including every 1 appliance increment within this range, for example, every 5 appliances 10.

Method of Use

The TMD appliance 10, or a series of TMD appliances 10, can be placed in an oral cavity as shown in FIG. 3.

The blocks 12, 14 can force the mandible forward, for example, due the interaction between the blocks 12, 14 when a person bites down on the blocks after the oral appliance is placed in the oral cavity.

The size and/or shape of the blocks 12, 14 can be configured to encourage a person to move their mandible forward with or without biting down on the blocks 12, 14. For example, the blocks 12, 14 can interact to move the mandible forward when a person bites down on the blocks 12, 14. However, a person can use the blocks 12, 14 with or without moving their mandible forward. The size and/or shape of the blocks 12, 14 can be configured to advance a person's mandible. The size and/or shape of the blocks 12, 14 can be configured to not advance a person's mandible.

The size and/or shape of the blocks 12, 14 can cause a mandible to advance from a retruded position, neutral position, or advanced position. The size and/or shape of the blocks 12, 14 can prevent, inhibit, or limit mandibular retrusion relative to a retruded position, neutral position, or advanced position of the mandible, whether such a position is a natural position of a person, or whether it is caused by the blocks 12, 14. In this way, the blocks 12, 14 can be configured to interact with one another to treat TMD by repositioning the jaw and/or by adjusting the bite. The blocks 12, 14 can also be configured to reshape and/or maintain the airway and prevent, inhibit, or limit the airway from partially and/or entirely closing to treat SBD, for example, from a partially or entirely open configuration. Such an arrangement can advantageously provide TMD and/or SBD treatment by repositioning the jaw and/or by opening up the airway.

As described above, one or more maxillary blocks 12 can cooperate with one or more mandibular blocks 14 to reposition the jaw, adjust the bite, and/or reshape and/or maintain the airway. FIG. 3 illustrates that the blocks 12, 14 can cooperate with one another to move the mandible forward. FIG. 3 also illustrates that the blocks 12, 14 can cooperate with one another to reshape the airway into one or more open configurations, for example, by increasing the interocclusal separation between maxillary and mandibular dentitions. The blocks 12, 14 can be designed to maintain the mandible in one or more forward positions when the blocks 12, 14 are engaged with one another. The blocks 12, 14 can also be designed to maintain the airway in one or more open configurations, including one or more reshaped configurations caused at least partially by the interaction of the blocks 12, 14. The blocks 12, 14 can interact with one another to reshape the airway by repositioning (also referred to as displacing) the mandible relative to the maxilla to treat TMD, or to additionally treat SBD, where the amount of mandibular advancement and/or the interocclusal separation can be the same or different when TMD and SBD are simultaneously being treated as compared to when only TMD is being treated. For example, the TMD appliance 10 can cause less interocclusal separation (e.g., about 1 mm to about 40 mm less interocclusal separation, including every 1 mm increment within this range, for example, 10 mm) when treating only TMD as opposed to concurrently treating TMD and SBD. As another example, the TMD appliance 10 can cause less mandibular advancement (e.g., about 1 mm to about 20 mm less mandibular advancement, including every 1 mm increment within this range, for example, 10 mm) when treating only TMD as opposed to concurrently treating TMD and SBD. For example, the blocks 12, 14 can be configured to move the mandible forward and/or increase the interocclusal separation between the maxillary and mandibular dental arches when the blocks 12, 14 interact with one another. Such displacement can advantageously reposition the jaw and adjust the bite—thus providing TMD treatment—can also advantageously reshape the airway and cause the airway to become more open—thus providing SBD treatment.

The blocks 12, 14 can interact with one another to adjust the bite by maintaining a neutral position (e.g., non-advanced position) or a displaced position (e.g., advanced position) of the mandible relative to the maxilla. The blocks 12, 14 can also interact with one another to maintain an open airway by maintaining a neutral position (e.g., non-advanced) or a displaced position (e.g., advanced position) of the mandible relative to the maxilla. For example, the blocks 12, 14 can prevent, inhibit, or limit posterior movement of the mandible and/or a reduction of the interocclusal distance when the mandible is in a neutral and/or displaced position. Such mandibular support can advantageously treat TMD by training the jaw to return to a new, or modified, neutral position. Such mandibular support can also advantageously prevent, inhibit, or limit the tongue from falling back and collapsing the airway. A neutral position is considered any natural occlusal position. A displaced position is considered any non-displaced position, for example, any advanced and/or retruded position, natural or imposed. The blocks 12, 14 can cause a displaced mandibular position to become a new natural occlusal position, for example, by orthodontically manipulating (e.g., progressively manipulating with a series of trays and/or blocks) craniofacial structures over time such that the mandible and associated structures acquire a new equilibrium (e.g., neutral) position.

The blocks 12, 14 can interact with one another to widen the maxillary (also referred to as superior or upper) dental arch and/or the mandibular (also referred to as inferior or lower) dental arch. For example, the blocks 12, 14 can have one or more transverse slopes that can interact with one another to widen the hard and/or soft palates. Such widening can advantageously reshape the airway and cause it to become more open. Widening the mandibular dental arch can increase the size of the sublingual space and decrease the amount of obstruction the tongue causes in the oral cavity. Widening the maxillary dental arch can cause palatal expansion and thereby increase the size of the oral cavity.

The blocks 12, 14 can interact to move the mandible forward, temporarily or permanently. The blocks 12, 14 can also interact to cause the airway to develop a more open configuration, temporarily or permanently. The blocks 12, 14 can be configured to temporarily or permanently manipulate craniofacial structures.

The one or more guide surface pairs 26-28 of the oral appliance 10 (e.g., pair 26a-28a and/or pair 26b-28b) can interact in such a manner to prevent, inhibit, or limit posterior movement of the mandible and associated structures (e.g., the tongue), for example, to treat TMD and/or SBD. The maxillary and mandibular guide surfaces 26, 28 can be configured to interact with one another or to otherwise contact each other throughout treatment or only during a portion thereof. As described above, the blocks 12, 14 can be configured to interact in a self-guided manner.

FIG. 3 illustrates that a cooperating pair of guide surfaces 26b, 28b can interact to advance the mandible into a forward position (also referred to as advanced). FIG. 3 also illustrates that such advancement can increase the interocclusal distance between the dental arches, but the TMD appliance 10 can advance the mandible without increasing the interocclusal distance as well. Where there is an increase in the interocclusal distance, the resultant interocclusal distance can be greater than the natural interocclusal distance that would otherwise result between the arches if the jaw were simply advanced without the use of guide surfaces 26, 28. For example, the resultant interocclusal distance can be greater than the natural interocclusal separation that the alignment of the anterior teeth causes when the mandible is advanced when clenched. Where the anterior teeth do not produce natural disclusion upon the advancement of the mandible, the resultant interocclusal distance that results can be due solely to one or more cooperating pairs of guide surfaces 26, 28 when the mandible is advanced.

FIG. 3 illustrates that the closing of the jaws with a cooperating pair of guide surfaces 26, 28 can advance the mandible forward an advancement distance 34. The advancement distance 34 can be from about 0 mm to about 30 mm, more narrowly from about 0 mm to about 20 mm, yet more narrowly from about 0 mm to about 10 mm, yet still more narrowly from about 5 mm to about 10 mm, including every 0.25 mm increment within these ranges, for example, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm. FIG. 3 illustrates that the cooperating pair of guide surfaces 26, 28 can advance the mandible forward a sufficient advancement distance 34 to artificially create an underbite (also referred to as a Class III malocclusion). For example, the cooperating pair of guide surfaces 26, 28 can advance the mandible forward such that the maxillary incisors are within the anterior perimeter (as opposed to posterior where the molars are) of the mandibular incisors by, for example, from about 0.5 mm to about 5.0 mm, including every 0.25 mm increment within this range.

The closing of the jaws with a cooperating pair of guide surfaces 26, 28 can increase the interocclusal distance 36 between the dental arches from about 0 mm to about 60 mm, more narrowly from about 0 mm to about 50 mm, more narrowly from about 0 mm to about 40 mm, yet more narrowly from about 0 mm to about 30 mm, yet still more narrowly from about 0 mm to about 20 mm, yet more narrowly still from about 0 mm to about 10 mm, including every 0.25 mm increment within these ranges, for example, about 30 mm, about 31 mm, about 32 mm, about 33 mm, about 34 mm, about 35 mm, about 36 mm, about 37 mm, about 38 mm, about 39 mm, about 40 mm. The range of natural disclusion can range from 0 mm to about 10 mm, including every 0.25 mm increment within this range. The interocclusal distance 36 can be the height $12_H$ of a maxillary block 12, the height $14_H$ of a mandibular block 14, or a combination thereof.

At least a portion of each pair of cooperating guide surfaces 26, 28 (e.g., guide surfaces 26b, 28b) can contact each other when the jaw is being closed, for example from an open configuration to a closed (or less open) configuration. At least a portion of each pair of opposing guide surfaces 26, 28 can slidably contact each other such that at least a portion of the guide surfaces 26, 28 slide past one another to advance the mandible and increase the interocclusal distance when the jaw is closed, for example, from an open configuration to a less open configuration. The cooperating guide surfaces can have a contact length that ranges from 0 mm when not in contact to about 1 mm to about 30 mm when in contact, including every 0.5 mm increment within this range. The contact length can increase from 0 mm to a maximum contact length as the mandible is closed against the maxilla, or equivalently, as the mandibular dentition is closed against the maxillary dentition. FIG. 3 illustrates that the cooperating guide surfaces 26, 28 can have a maximum contact length of about 3 mm to about 15 mm, including every 0.5 mm increment within this range, for example, 12 mm. The maximum contact length can be the entire length or only part of the length of one or both of the cooperating guide surfaces 26, 28. FIG. 3 illustrates that the maximum contact length can be the length of the maxillary guide surfaces 26. Alternatively or additionally, at least a portion of each pair of opposing guide surface 26, 28 can be configured to not slidably contact each other, but rather merely rest against each another when the jaw is open to prevent, inhibit, or limit retrusion of the mandible.

For example, when the jaws are partially or fully closed, at least a portion of each pair of cooperating guide surfaces 26, 28 (e.g., guide surfaces 26b, 28b) can contact its opposing guide surface such that at least one of the guide surfaces 26, 28 prevents, inhibits, or limits posterior movement of the mandible. For example, FIG. 3 illustrates that the maxillary second guide surface 26b can interfere with (e.g., prevent, inhibit, or limit) any posterior movement of the mandibular second guide surface 28b, thereby interfering with any posterior movement of the mandibular second block 14b and the mandible.

The maxillary and mandibular blocks 12, 14 can cooperate to allow the mandible to move in multiple directions when the jaws are in a fully closed position, for example, side-to-side, front-to-back, and/or up-and-down (or in any three mutually orthogonal reference planes). For example, the blocks 12, 14 can have a movement tolerance of about 1 mm to about 5 mm (e.g., including every 0.25 mm increment within this range) along three or fewer reference planes/axes to advantageously maximize comfort, reduce the likelihood of the TMD device 10 from causing new TMD issues, minimize sleep bruxism, and/or inhibit the blocks 12, 14 from becoming dislodged while concurrently treating TMD, SBD, and/or snoring. The posterior guide surface of a posterior-anterior guide surface pair can, for example, resist but allow posterior movement of the anterior guide surface. The posterior and anterior guide surfaces can be any two opposing surfaces, for example, the maxillary second guide surface 26b and the mandibular second guide surface 28b pair, with the maxillary second guide surface 26b being posterior to the mandibular second guide surface 28b. Alternatively or additionally, the posterior guide surface can freely allow posterior movement of the anterior guide surface over the tolerance range and then begin to resist further posterior movement. For example, the posterior and anterior guide surfaces (e.g., posterior guide surfaces 26 and anterior guide surfaces 28) can be partially or entirely coated with the coating described above. The maxillary and mandibular guide surface angles 30, 32 can have angles that self-guide the mandible to return to a more forward position when the mandible moves posteriorly. The maxillary and mandibular blocks 12, 14 can cooperate to allow the mandible to have six degrees of freedom when the jaw is being opened and closed. The maxillary and mandibular blocks 12, 14 can be locked together when the mandible is in an advanced position, and allow movement within the tolerance range within one, two, three, four, five, and/or six degrees of freedom. The maxillary and mandibular blocks 12, 14 can be attached to one another (e.g., a maxillary block 12 can be attached to a mandibular block 14), for example, via an interference fit (also referred to as a friction fit), snap fit, a tether, band, elastic band, hook, elastic hook, or any combination thereof, with or without one, two, three, four, five, and/or six degrees of freedom. For example, the maxillary blocks 12 can have a protrusion and the mandibular blocks 14 can have a recess configured to receive the protrusion via an interference fit or a snap fit.

Alternatively or additionally, the TMD appliances 10 disclosed herein can allow free mandibular motion except for the retrusion prevented, inhibited, or limited by two opposed guide surface pairs 26, 28 when they are in a position to interact with one another.

As described above, a series of blocks 12, 14 can be designed and applied or used over time to move one or more teeth, advance and/or maintain a position of the mandible, increase the interocclusal distance 36 and/or widen the hard and/or soft palates in two or more successive steps in a series. Exemplary dimensional variations are disclosed below, but these are in no way limiting, as every permutation of the dimensions and relative positions herein disclosed is appreciated, for example, including every 0.25 mm increment or 0.5% increment within the dimensional ranges disclosed herein. Successive dimensional changes can advantageously achieve the desired treatment in each step in a series. Each block 12, 14 in a series can have guide surface angles 30, 32 that correspond to an intermediate or end mandible advancement position or interocclusal distance intended for the block 12, 14 in the series. Each block 12, 14 in a series can have block lengths, widths and heights $12_L$, $14_L$, $12_w$, $14_w$, $12_H$, $14_H$ that correspond to an intermediate or end mandible advancement position or interocclusal distance intended for the block 12, 14 in the series. Each block 12, 14 in a series can have guide surface lengths $26_L$, $28_L$ that correspond to an intermediate or end mandible advancement position or interocclusal distance intended for the block 12, 14 in the series.

Each block 12, 14 in a series can be configured to contact a different portion or a length of a guide surface of an opposing block. Each block 12, 14 in a series can have a longitudinal and/or transverse slope that corresponds to an intermediate or end mandible advancement position or interocclusal distance intended for the block 12, 14 in the series. One or more of the dimensions disclosed can be increased, decreased, or remain unchanged from one treatment step to the next treatment step (i.e., one or more dimensions can remain unchanged between two treatment steps). For example, one or more dimensions can be increased and/or decreased from a first dimension to a second dimension between two treatment steps (e.g., between a first treatment step and a second treatment step with no treatment step between the first and second treatment steps, or between any two treatment steps) such that the second dimension is about 0.5 mm to about 40 mm greater than or less than the value of the first dimension in the first treatment step than in the second (e.g., subsequent) treatment step, for example, every 0.25 mm increment between 0.5 mm and 40 mm (e.g., 0.5 mm, 1.0 mm, 1.5 mm, 2.0 mm, 2.5 mm, 3.0 mm, 3.5 mm, 4.0 mm, 4.5 mm, 5.0 mm and so on). For example, one or more dimensions can be increased and/or decreased from a first dimension to a second dimension between two treatment steps (e.g., between a first treatment step and a second treatment step with no treatment step between the first and second treatment steps, or between any two treatment steps) such that the second dimension is about 1% to about 500% greater than or less than the value of the first dimension in the first treatment step than in the second (e.g., subsequent) treatment step, for example, every 1% increment between 1% and 500% (e.g., 1%, 5%, 10%, 15%, 20%, 25%, 30%, 40%, 45%, 50%, 55%, 60%, 65%, 70%, 75%, 80%, 85%, 90%, 95%, 100%, 125%, 150%, 175% and so on).

In a treatment series, the blocks 12, 14 can move one or more teeth, reposition the mandible, adjust the bite, adjust the interocclusal distance, and/or widen the hard and/or soft palates to an intermediate or end arrangement as desired in one or more treatment steps in a series. The blocks 12, 14 can progressively move teeth, increase and/or decrease the advancement distance 34, increase and/or decrease the interocclusal distance 36, widen the hard and/or soft palates, adjust the bite, or any combination thereof. For example, the blocks 12, 14 in a series can progressively increase the advancement distance 34 from a first distance to a second distance greater than the second distance. The blocks 12, 14 in a series can progressively decrease the advancement distance 34 from the second distance to a third distance less than the second distance and greater than the first distance. As another example, the blocks 12, 14 in a series can progressively increase the interocclusal distance 36 from a first distance to a second distance greater than the first distance. The blocks 12, 14 in a series can progressively decrease the interocclusal distance 36 from the second distance to a third distance less than the second distance and greater than the first distance. As another example, the blocks 12, 14 in a series can progressively increase the width of a palate from a first width to a second width greater than the first width. The design of a series of blocks can advantageously reduce the initial shock of treatment to the affected craniofacial (e.g., mandible, dental arches, airway, palate) structures potentially caused by the blocks 12, 14 and therefore make the treatment more comfortable. Exemplary dimensional variations are disclosed below, but these are in no way limiting, as every permutation of the dimensions and relative positions herein disclosed is appreciated, for example, including every 0.25 mm increment or 0.5% increment within the dimensional ranges disclosed herein. One or more of the dimensions disclosed can be increased, decreased, or remain unchanged from one treatment step to the next treatment step (i.e., one or more dimensions can remain unchanged between two treatment steps). Such craniofacial dimensions (e.g., dimensions 34 and 36) can be increased and/or decreased from a first dimension to a second dimension between two treatment steps (e.g., between a first treatment step and a second treatment step with no treatment step between the first and second treatment steps, or between any two treatment steps) such that the second dimension is about 0.5 mm to about 40 mm greater than or less than the value of the first dimension in the first treatment step than in the second (e.g., subsequent) treatment step, for example, every 0.5 mm increment between 0.5 mm and 40 mm (e.g., 0.5 mm, 1.0 mm, 1.5 mm, 2.0 mm, 2.5 mm, 3.0 mm, 3.5 mm, 4.0 mm, 4.5 mm, 5.0 mm and so on). Such craniofacial dimensions (e.g., dimensions 34 and 36) can be increased and/or decreased from a first dimension to a second dimension between two treatment steps (e.g., between a first treatment step and a second treatment step with no treatment step between the first and second treatment steps, or between any two treatment steps) such that the second dimension is about 1% to about 500% greater than or less than the value of the first dimension in the first treatment step than in the second (e.g., subsequent) treatment step, for example, every 1% increment between 1% and 500% (e.g., 1%, 5%, 10%, 15%, 20%, 25%, 30%, 40%, 45%, 50%, 55%, 60%, 65%, 70%, 75%, 80%, 85%, 90%, 95%, 100%, 125%, 150%, 175% and so on).

Figure 5:
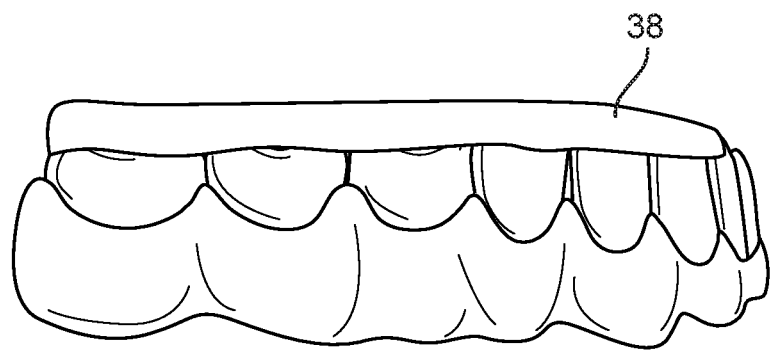
FIG. 5 illustrates a schematic of a variation of an aligner on teeth.

FIG. 5 illustrates a variation of an aligner 38 on teeth. The aligner 38 can have the properties of the oral trays described herein. For example, the aligner 38 can be a maxillary dentition aligner 38a or a mandibular dentition aligner 38b. The aligner 38 can have an inner surface and an outer surface. The inner surface can define a tooth-receiving cavity. The inner surface can be configured to contact one or more teeth. The inner surface can have a geometry configured to move one or more maxillary or mandibular teeth from a first position to a second position, for example, by exerting a force on one or more teeth (e.g., from an interference fit configured to move one or more teeth). The aligner 38 can fit over all or a subset of teeth in the maxillary and/or mandibular dentition.

A series of aligners 38 (e.g., maxillary and/or mandibular aligners 38a, 38b) can be designed and applied or used over time in order to reposition one or more maxillary and/or mandibular teeth in two or more successive steps, for example, as disclosed in PCT Publication WO 2016/004415 and U.S. application Ser. No. 15/386,280 (published as US 2017/0100214), both of which have been incorporated herein by reference in their entireties for all purposes. As described above, each aligner 38 in a series can have an inner surface that has a geometry that corresponds to an intermediate or end tooth arrangement intended for each aligner 38 in the series. The aligners 38 can be sufficiently resilient to accommodate or conform to misaligned teeth, but apply sufficient force against the misaligned teeth to reposition the teeth to the intermediate or end arrangement as desired for the particular treatment step. A series of aligners 38 can have geometries selected to progressively reposition teeth from a first arrangement through one or more successive intermediate arrangements to a final arrangement.

TMD appliance therapy can be combined with orthodontic aligner treatment as described above, for example, with an aligner 38 (e.g., a maxillary and/or mandibular aligner 38a, 38b). As further described above, one or more craniofacial adjustment blocks 12 and/or 14 (also referred to as guides and TMD components) can be directly or indirectly attached to or integrated with an aligner 38 (e.g., a maxillary and/or mandibular aligner 38a, 38b). The one or more maxillary blocks 12 can be monolithically formed with a maxillary aligner 38a. The one or more mandibular blocks 14 can be monolithically formed with a mandibular aligner 38a.

Figure 6:
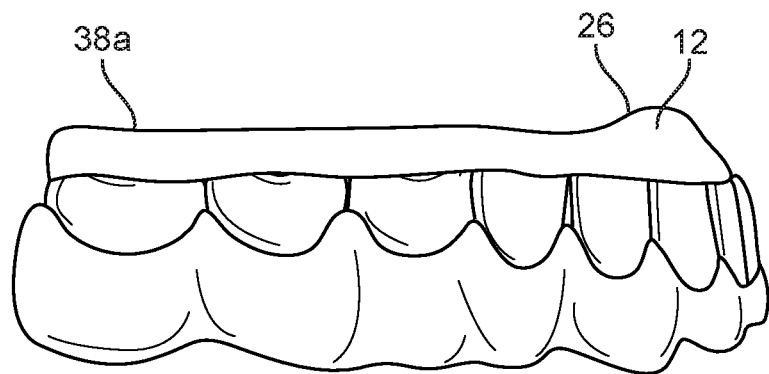
FIG. 6 illustrates a schematic of a variation of a maxillary aligner on teeth that has a variation of a craniofacial adjustment block.

FIG. 6 illustrates that a maxillary aligner 38a can have a maxillary guide 12 that has a guide surface 26. The guide 12 can be on an anterior or posterior portion of the maxillary aligner 38a. For example, FIG. 6 illustrates that the guide 12 can be on an anterior portion of the aligner 38a. The guide 12 can be one of the block 12, 14 described above with reference to FIGS. 1-3, and can be integrated with the aligner 38a as shown in FIG. 6.

Figure 7:
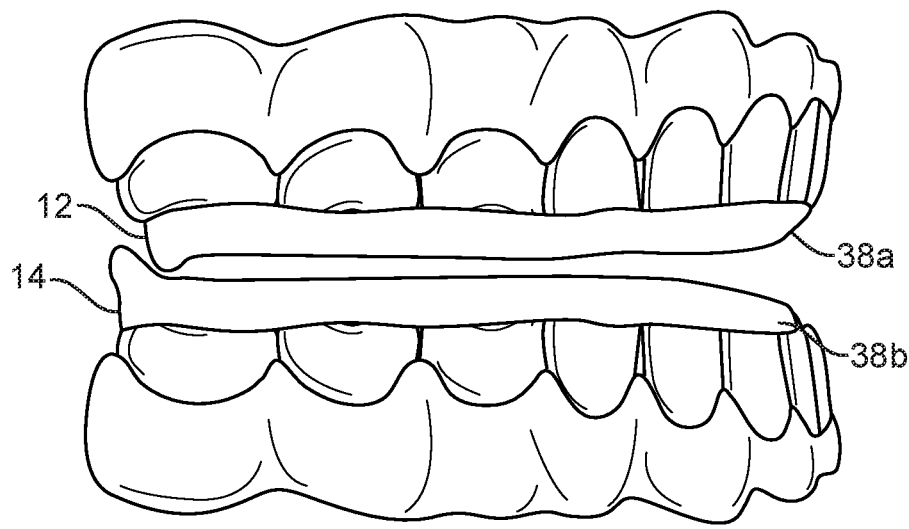
FIG. 7 illustrates a schematic of a variation of maxillary and mandibular aligners on teeth with each having a variation of a craniofacial adjustment block.

FIG. 7 illustrates that the guide 12 can be on a posterior portion of the aligner 38a. The aligner 38a can advantageously orthodontically move teeth concurrently with treating TMD and/or SBD, for example, by interacting with a mandibular aligner 38b. For example, FIG. 7 illustrates a jaw in a closed position having a maxillary aligner 38a and a mandibular aligner 38b with posterior guides 12, 14, where the posterior guides 12, 14 are interacting to keep the jaw in a closed position with more space between the upper and lower dentition than would otherwise occur without the posterior guides 12, 14. The guides 12, 14 can be the blocks 12, 14 described above with reference to FIGS. 1-3, and can be integrated with the aligners 38a, 38b, respectively, as shown in FIG. 7.

FIGS. 1-3, 6 and 7 each illustrate TMD components comprising angled surfaces and disclusion ramps such as craniofacial adjustment blocks 12, 14 that can be combined with the aligner 38 in FIG. 5 to concurrently provide TMD treatment along with the orthodontic movement of teeth. However, all types of TMD appliance therapy can be combined with orthodontic aligner treatment shown in FIG. 5, including other mandibular advancement appliances (e.g., Herbst appliances, elastic mandibular advancement (EMA) appliances), as well as, for example, stabilization splints (e.g., nightguards, day guards), deprogrammers (e.g., anterior deprogrammers), flat planes, and full contact splints with anterior guidance. For example, the aligner 38 can be combined with, attached to, removably attached to, or integrated with these other types of TMD components. The aligner 38 can replace the teeth (e.g., occlusal) engagement portions of these other types of TMD components so that each appliance 10 can orthodontically move teeth in addition to providing TMD treatment. Such orthodontic/TMD appliances can advantageously orthodontically move the teeth into a position that is physiologically correct for the TMJ and musculature during TMD treatment with a TMD appliance. The maxillary and mandibular aligner components and/or the TMD components of these oral appliances 10 can comprise a thermoplastic material that can, for example, be thermoformed with the aid of a computer program.

The aligners described herein can form a friction fit with the dentition. The friction fit can be non-uniformly spread across the aligners to apply different forces to different teeth, thereby enabling different teeth to be orthodontically moved by different amounts, with the amounts being proportionate to the various (e.g., different) forces applied across the dentition.

Two sets of oral appliances 10 can be made for every stage of treatment: one for daytime use and one for nighttime use. The daytime oral appliances 10 can orthodontically move teeth. The daytime oral appliances can provide TMD treatment. For example, the daytime oral appliances 10 can have a TMD component that is smaller than the nighttime oral appliances 10, or the daytime oral appliances 10 can omit the TMD component altogether. The nighttime oral appliances 10 can concurrently treat TMD and orthodontically move teeth. The nighttime oral appliances can have a TMD component. . Each daytime oral appliance 10 in a series can be designed to open and/or advance the lower jaw less than the corresponding nighttime oral appliance 10 in the series, or not at all. The daytime and nighttime appliances can have the same corresponding stage of orthodontic treatment. The daytime stage of orthodontic treatment can be less aggressive (e.g., apply less force to the teeth) than the nighttime stage of orthodontic treatment. Alternatively or additionally, only one series of oral appliances 10 can be made for every step of treatment (as opposed to two parallel series of appliances—one for day use and one for night use). For example, one or more of the locked configurations of the appliance 10 in each step of a series can be for daytime use and one or more of the locked configurations of the appliance 10 in each step of a series can be for nighttime use.

Figure 8:
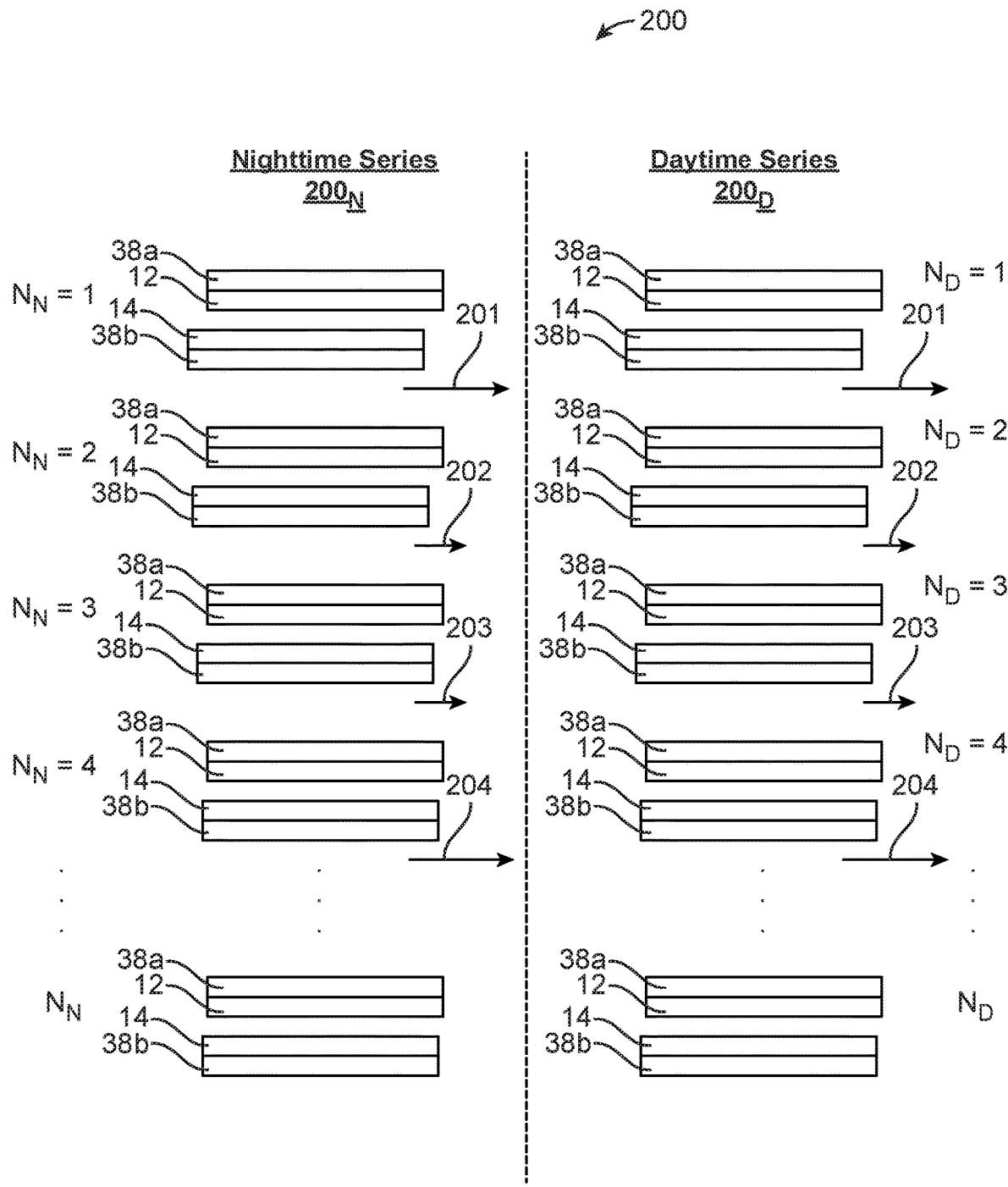
FIG. 8 illustrates a schematic of a variation of a series of oral appliances.

FIG. 8 illustrates a schematic of a variation of a series 200 of oral appliances 10. The oral appliance series 200 can have $N_D$ daywear oral appliances 10 in a daytime series $200_D$ and/or can have $N_N$ nightwear oral appliances 10 in a nighttime series $200_N$, where $N_D$ and $N_N$ can each be between 1 and 100, including every increment of 1 within this range. $N_D$ can be the same or different from $N_N$. The dimensions of the daytime and nighttime oral appliances 10 in each step of the series 200 can be the same or different than one another. The daytime and nighttime oral appliances 10 in each step of the series 200 can advance the jaw as described above, for example, by the same amount. For example, FIG. 8 illustrates that steps 1-4 of the series 200 can each progressively move the jaw forward by about 1.0 mm, by about 0.5 mm, by about 0.5 mm, and by about 1.0 mm, respectively, which is represented in FIG. 8 by arrows 201, 202, 203, and 204, respectively. FIG. 8 illustrates the relative positions of the maxillary aligner and TMD components (e.g., aligner 38a and TMD components 12) relative to the mandibular aligner and TMD components (e.g., aligner 38b and TMD components 14).

Method of Making

Figure 9:
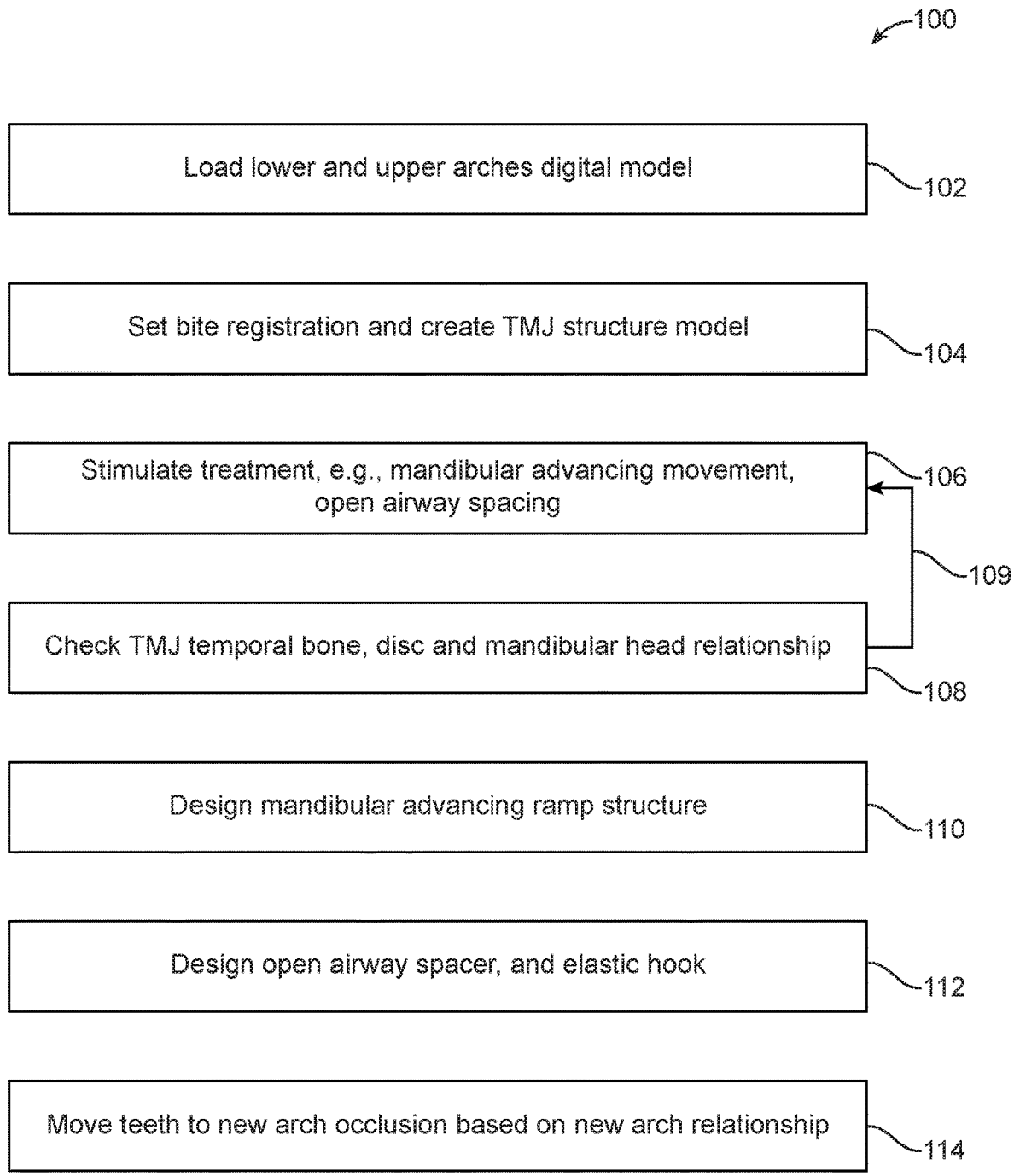
FIG. 9 illustrates a variation of a process for making a variation of an oral appliance.

FIG. 9 illustrates a variation of a process 100 of making the oral appliance 10. A computer program can be used to retrieve data from data acquisition devices (e.g., oral scanners, x-ray devices, cameras) to record and measure orthodontic malocclusions and teeth misalignments. Step 102 illustrates that after a digital model of the dentition is obtained, the digital models for the lower and upper arches can be loaded, e.g., into a computer. Step 104 illustrates that the bite registration can be set and a temporomandibular joint (TMJ) model can be created. The desired treatment can be simulated in step 106, including, for example, mandibular advancement, palatal expansion, teeth movement, or any combination thereof. The TMJ temporal bone, disc and mandibular head relationship can be checked in step 108, for example, when mandibular advancement is simulated in step 106. If the check is satisfactory, the process can move on to step 110, otherwise the process can return to step 106 and run one or more additional simulations. Based at least partly on the simulation(s) and check(s) in steps 106 and 108, an algorithm can be configured to design one or more aspects of the TMD components (e.g., guide surfaces 26, 28) in step 110 to effect the desired mandibular advancement. Step 112 illustrates that the blocks 12, 14 and/or oral trays can be designed that have the guide surfaces 26, 28 designed in step 110. Step 112 also illustrates that an optional elastic hook can be designed to prevent the jaw from opening and moving away from the maxillary blocks 12 when a person is sleeping. Step 114 illustrates that the blocks 12, 14 and/or oral trays designed in step 112 can move one or more teeth to a new arch occlusion based on a new arch relationship at least partly determined by the algorithm. The process 100 can be used to create one oral appliance 10 or a series of oral appliances 10.

Software can be used to manipulate digital impressions (scans) of the dental arches to incrementally move the teeth as well as designing the functional applications for daytime and/or nighttime use on a 3D printed model for appliance fabrication utilizing traditional vacu-form technique or direct to print appliances.

Using the process 100 in FIG. 9, an oral appliance 10 and/or a series of oral appliances 10 can be designed by the computer algorithm based on data the algorithm receives and processes from one or multiple data acquisition devices (e.g., scanners, x-ray devices, cameras) that can individually or collectively form a digital impression of an oral cavity and the dentition therein. For example, the dimensions of the oral appliance 10 in each step, including the TMD components (e.g., maxillary and mandibular blocks 12, 14, or one or more aspects thereof, including the oral trays) and/or the aligner components (e.g., maxillary and mandibular aligners 38a, 38b) can be determined from data received from the data acquisition devices. The algorithm in process 100 can combine orthodontic aligners with multiple different discipline TMD treatments, for example, to adjust the bite, restore some or all of the teeth, and move the teeth into a more desirable position.

For example, the data retrieved from the data acquisition devices can be used to measure orthodontic malocclusions, determine orthodontic corrections for the malocclusions while simultaneously treating TMD, for example, by designing a series of oral appliances 10 that can progressively treat TMD concurrently with a progressive orthodontic movement of teeth. Computer software can be used to determine the orthodontic movements of the teeth in one or more steps of a series. Computer software can be used to design the appliances 10. Computer software can be used to manufacture 3D models or directly print appliances 10. Models of the appliances 10 can be created by using computer software to incrementally move the teeth digitally and then print a 3D model from which an orthodontic aligner can be fabricated. Alternatively or additionally, the aligners can be fabricated directly with a 3D printer using computer software. The orthodontic aligner can be altered or otherwise modified on the occlusal surface to create the desired TMD treatment appliance 10 while the orthodontic movement is concurrently occurring. Giving the dentist or orthodontist the ability to treat TMD simultaneously with the orthodontic movement of teeth via a computer program that converts data received from one or more data acquisition devices into a series of successive orthodontic/TMD appliances 10 can advantageously open up many new treatment protocols for dentists and orthodontists to use to serve their patients. Such orthodontic/TMD appliances 10 can limit or reduce the need for surgery and restorative dental work (often times extensive or significant) that is typically occurs when TMD is treated with TMD appliances without the concurrent orthodontic movement of teeth. The orthodontic/TMD appliances 10 disclosed herein avoid such drawbacks of solo TMD appliances by orthodontically moving the teeth into a position which is physiologically correct for the TMJ and musculature.

The claims are not limited to the exemplary embodiments shown in the drawings, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

What is claimed is:

1. An oral appliance for the combined orthodontic movement of teeth and treatment of temporomandibular joint dysfunction (TMD), comprising:
    a first orthodontic aligner;
    a second orthodontic aligner; and
    a TMD treatment device, comprising:
        a first guide having a first angled guide surface positioned along the first orthodontic aligner; and
        a second guide having a second angled guide surface positioned along the second orthodontic aligner, the second angled guide surface having a second angled guide surface length,
    wherein when the first orthodontic aligner is worn by a user, the first angled guide surface is between a buccal side and a lingual side of a first maxillary tooth,
    wherein when the second orthodontic aligner is worn by the user, the second angled guide surface is between a buccal side and a lingual side of a first mandibular tooth,
    wherein when the first and second orthodontic aligners are worn by the user and the user's lower jaw is in a fully closed position such that the first and second angled guide surfaces are in contact with one another and such that the second guide is pressed against a portion of the first orthodontic aligner that extends between a buccal side and a lingual side of a second maxillary tooth, the first and second guides are in a fully engaged configuration,
    wherein when the first and second guides are in the fully engaged configuration, the first guide is opposed to the second guide,
    wherein when the first and second guides are in the fully engaged configuration, the first guide has a free surface positioned to not contact the second guide such that a gap is defined between the free surface and the second guide, the free surface having a free surface length, the free surface length being less than the second angled guide surface length,
    wherein when the first and second guides are in the fully engaged configuration, the free surface is between a buccal side and a lingual side of a second mandibular tooth,
    wherein when the first and second guides are in the fully engaged configuration, the free surface faces the second guide surface, and
    wherein the oral appliance is configured to concurrently reposition a mandible and orthodontically move one or more teeth, and wherein the second guide surface is at a constant angle relative to the free surface.

2. The oral appliance of claim 1, wherein the TMD treatment device comprises at least one of a mandibular advancement appliance, a stabilization splint and a deprogrammer.

3. The oral appliance of claim 1, wherein the oral appliance further comprises one or more locking mechanisms configured to restrict movement of the mandible when the one or more locking mechanisms are engaged with one another.

4. The oral appliance of claim 3, wherein the mandible is allowed to move in one, two, three, four, five, or six degrees of freedom when the one or more locking mechanisms are engaged with one another.

5. The oral appliance of claim 3, wherein the mandible is allowed to translate along one, two, or three axes when the one or more locking mechanisms are engaged with one another.

6. The oral appliance of claim 5, wherein the mandible is allowed to translate from 0.5 mm to 10.0 mm along one or more of the one, two, or three axes when the one or more locking mechanisms are engaged with one another.

7. The oral appliance of claim 3, wherein the one or more locking mechanisms comprise at least one of clasps, clips, hooks, elastic hooks, barbs, spurs, fasteners, elastic bands, interlocking male and female components.

8. A system for the combined orthodontic movement of teeth and treatment of temporomandibular joint dysfunction (TMD), comprising:

a series of oral appliances configured to concurrently reposition both a mandible and orthodontically move one or more teeth, wherein each oral appliance in the series comprises:
a first orthodontic tray and a second orthodontic tray, wherein the first and second orthodontic trays comprise a TMD treatment device, the TMD treatment device comprising:
a first guide that extends from the first orthodontic tray, wherein the first guide has a first angled guide surface, a first guide base, and a free surface, and wherein the free surface is opposite the base; and
a second guide that extends from the second orthodontic tray, wherein the second guide has a second angled guide surface, a second guide base, and a surface angled relative to the second angled guide surface, and wherein the second guide base is opposite the surface angled relative to the second angled guide surface,
wherein when the first and second guides are in contact with one another and the first guide base and the surface angled relative to the second angled guide surface are in the same plane, the first guide is opposed to the second guide and the first angled guide surface is in contact with a first portion of the second angled guide surface,
wherein when the first and second guides are in contact with one another and the first guide base and the surface angled relative to the second angled guide surface are in the same plane, the free surface does not contact the second guide such that a gap is defined between the free surface and the second guide,
wherein when the first and second guides are in contact with one another and the first guide base and the surface angled relative to the second angled guide surface are in the same plane, the free surface faces a second portion of the second angled guide surface, and
wherein the first and second portions of the second angled guide surface are at the same angle relative to the free surface, and wherein the first and second guides are located between buccal and lingual sides of maxillary and mandibular teeth, respectively.

9. The system of claim 8, wherein the series comprises 2 to 100 oral appliances.

10. The system of claim 8, wherein each oral appliance in the series is configured to progressively reposition one or more maxillary teeth and/or one or more mandibular teeth.

11. The system of claim 8, wherein one or more oral appliances in the series is configured to progressively advance the mandible by 0.25 mm or by 0.5 mm.

12. The system of claim 8, wherein each oral appliance in the series is configured to progressively advance the mandible by 0.25 mm or by 0.5 mm.

13. The system of claim 8, wherein the TMD treatment device comprises at least one of a mandibular advancement appliance, a stabilization splint and a deprogrammer.

14. The system of claim 8, wherein one or more of the TMD treatment devices in the series comprises one or more locking mechanisms configured to restrict movement of the mandible when the one or more locking mechanisms are engaged with one another.

15. The system of claim 14, wherein the mandible is allowed to translate along one, two, or three axes when the one or more locking mechanisms are engaged with one another.

16. The system of claim 15, wherein the mandible is allowed to translate from 0.5 mm to 10.0 mm along one or more of the one, two, or three axes when the one or more locking mechanisms are engaged with one another.

17. The system of claim 8, wherein the series of oral appliances comprises a first oral appliance having first oral appliance dimensions and a second oral appliance having second oral appliance dimensions, wherein one or more of the second oral appliance dimensions are greater than or less than one or more of the first oral appliance dimensions.

18. The system of claim 17, wherein one or more of the second oral appliance dimensions are greater than or less than one or more of the first oral appliance dimensions by 1% to 500% or by 0.5 mm to 10.0 mm.

19. A method of progressively treating temporomandibular joint dysfunction (TMD), comprising:
providing a series of oral appliances configured to concurrently reposition both a mandible and orthodontically move one or more teeth, wherein each oral appliance in the series comprises:
a first orthodontic tray;
a second orthodontic tray; and
a TMD treatment device, comprising:
a first guide having a first angled guide surface positioned along the first orthodontic tray, the first guide extending from the first orthodontic tray; and
a second guide having a second angled guide surface positioned along the second orthodontic tray, the second guide extending from the second orthodontic tray,
wherein when the first orthodontic tray is worn by a user, the first angled guide surface is between a buccal side and a lingual side of a first maxillary tooth,
wherein when the second orthodontic tray is worn by the user, the second angled guide surface is between a buccal side and a lingual side of a first mandibular tooth,
wherein when the first and second orthodontic trays are worn by the user and the user's lower jaw is in a fully closed position such that the first and second angled guide surfaces are in contact with one another and such that the second guide is pressed against a portion of the first orthodontic tray that extends between a buccal side and a lingual side of a second maxillary tooth, the first and second guides are in a fully engaged configuration,
wherein when the first and second guides are in the fully engaged configuration, the first guide is opposed to the second guide,
wherein when the first and second guides are in the fully engaged configuration, the first guide has a free surface positioned to not contact the second guide such that a gap is defined between the free surface and the second guide,
wherein when the first and second guides are in the fully engaged configuration, the free surface is opposite the second angled guide surface, and
wherein when the first and second guides are in the fully engaged configuration, the free surface is between a buccal side and a lingual side of a second mandibular tooth and wherein the second angled guide surface is at a constant angle relative to the free surface.

20. The method of claim 19, wherein the series comprises 2 to 100 oral appliances, and wherein the TMD treatment device comprises at least one of a mandibular advancement appliance, a stabilization splint and a deprogrammer.

21. The oral appliance of claim 1, wherein the first guide has a first guide height, wherein the free surface defines an apex of the first guide height,
   wherein the free surface has a free surface proximal terminal end and a free surface distal terminal end, wherein when the first and second guides are in the fully engaged configuration, the free surface proximal terminal end is closer to a front of the user's mouth than the free surface distal terminal end,
   wherein the second guide angled surface has a second guide angled surface proximal terminal end and second guide angled surface distal terminal end, wherein when the first and second guides are in the fully engaged configuration, the second guide angled surface proximal terminal end is closer to a front of the user's mouth than the second guide angled surface distal terminal end,
   wherein when the first and second guides are in the fully engaged configuration first, the second guide angled surface proximal terminal end is closer to maxillary teeth than the second guide angled surface distal terminal end, wherein when the first and second guides are in the fully engaged configuration, the second guide angled surface distal terminal end is closer to mandibular teeth than the second guide angled surface proximal terminal end,
   wherein when the first and second guides are in the fully engaged configuration, the free surface distal terminal end is distal of the second guide angled surface distal terminal end such that the free surface distal terminal end is further from the front of the user's mouth than the second guide angled surface distal terminal end, and
   wherein when the first and second guides are in the fully engaged configuration, the free surface proximal terminal end and the free surface distal terminal end are both distal to the second angled guide surface proximal terminal end.

22. The oral appliance of claim 21, wherein the second guide has a second guide height, and wherein the first guide height is less than the second guide height.

23. The oral appliance of claim 21, wherein the second guide has a second guide height, wherein when the first and second guides are in the fully engaged configuration, the second guide height is measured between a mandibular tooth surface and an apex of the second guide, wherein when the first and second guides are in the fully engaged configuration, the apex of the first guide height is between the mandibular tooth surface and a maxillary tooth surface, and wherein when the first and second guides are in the fully engaged configuration, the apex of the first guide height is between the mandibular tooth surface and the apex of the second guide.

24. The system of claim 8, wherein the first guide has a first guide height, and wherein the free surface defines an apex of the first guide height.

25. The system of claim 8, wherein the first angled guide surface has a first angled guide surface length, wherein the second angled guide surface has a second angled guide surface length, and wherein the first angled guide surface length is less than the second angled guide surface length.

26. The system of claim 8, wherein when the first and second guides are in contact with one another, the second angled guide surface extends away from the free surface.

27. The system of claim 8, wherein the free surface has a free surface first end and a free surface second end, and wherein when the first and second guides are in contact with one another, the free surface first end is closer to the second angled guide surface than the free surface second end.

28. The oral appliance of claim 1, wherein when the first and second guides are in the fully engaged configuration, the first angled guide surface is in contact with a first portion of the second angled guide surface and the free surface faces a second portion of the second angled guide surface, and wherein the first and second portions of the second angled guide surface are at the same angle relative to the free surface.

29. The oral appliance of claim 1, wherein when the first and second guides are in the fully engaged configuration, the first angled guide surface is in contact with a first portion of the second angled guide surface and the free surface faces a second portion of the second angled guide surface, and wherein the first and second portions of the second angled guide surface are at the same angle relative to each other.

30. The oral appliance of claim 1, wherein when the first and second guides are in the fully engaged configuration, the first angled guide surface is in contact with a first portion of the second angled guide surface and the free surface faces a second portion of the second angled guide surface, and wherein the first and second portions of the second angled guide surface are at the same angle relative to a surface of the first maxillary tooth, to a surface of the second maxillary tooth, to a surface of the first mandibular tooth, or to a surface of the second mandibular tooth.

31. The system of claim 8, wherein when the first and second orthodontic trays are worn by a user and the user's lower jaw is in a fully closed position such that the first and second angled guide surfaces are in contact with one another and such that the second guide is pressed against a portion of the first orthodontic tray that extends between a buccal side and a lingual side of a maxillary tooth, the first and second guides are in a fully engaged configuration,
   wherein when the first and second guides are in the fully engaged configuration, the second angled guide surface extends away from the free surface,
   wherein the free surface has a free surface first end and a free surface second end, and
   wherein when the first and second guides are in the fully engaged configuration, the free surface first end is closer to the second angled guide surface than the free surface second end.

32. The system of claim 31, wherein when the first and second guides are in the fully engaged configuration, the first portion of the second angled guide surface extends away from the free surface in a first direction and the second portion of the second angled guide surface extends away from the free surface in a second direction opposite the first direction.

* * * * *